US010675058B2

(12) United States Patent
Prior et al.

(10) Patent No.: US 10,675,058 B2
(45) Date of Patent: Jun. 9, 2020

(54) DEVICES, SYSTEMS, AND METHODS FOR LARGE TISSUE SPECIMEN REMOVAL

(71) Applicant: COVIDIEN LP, Mansfield, MA (US)

(72) Inventors: Scott J. Prior, Shelton, CT (US); Nikolai D. Begg, Wayland, MA (US); Danial P. Ferreira, Milford, CT (US); Paul C. Di Cesare, Shelton, CT (US); Walter S. Shunaula, West Haven, CT (US)

(73) Assignee: Covidien LP, Mansifled, MA (US)

( * ) Notice: Subject to any disclaimer, the term of this patent is extended or adjusted under 35 U.S.C. 154(b) by 164 days.

(21) Appl. No.: 15/867,888

(22) Filed: Jan. 11, 2018

(65) Prior Publication Data

US 2018/0199961 A1   Jul. 19, 2018

Related U.S. Application Data

(60) Provisional application No. 62/515,622, filed on Jun. 6, 2017, provisional application No. 62/461,488, filed on Feb. 21, 2017, provisional application No. 62/448,266, filed on Jan. 19, 2017.

(51) Int. Cl.
*A61B 17/42* (2006.01)
*A61B 17/34* (2006.01)
*A61B 17/29* (2006.01)
*A61B 17/32* (2006.01)
*A61B 17/00* (2006.01)
*A61B 90/00* (2016.01)
*A61B 17/04* (2006.01)
*A61B 18/14* (2006.01)

(52) U.S. Cl.
CPC ........ *A61B 17/42* (2013.01); *A61B 17/00234* (2013.01); *A61B 17/32002* (2013.01);
(Continued)

(58) Field of Classification Search
CPC . A61B 17/42; A61B 17/3421; A61B 17/3423; A61B 2017/00287
See application file for complete search history.

(56) References Cited

U.S. PATENT DOCUMENTS 5,352,184 A * 10/1994 Goldberg ............... A61B 10/04
128/DIG. 24
5,556,376 A * 9/1996 Yoon ................ A61B 17/00234
604/11
(Continued)

FOREIGN PATENT DOCUMENTS

EP   1967146 A2   9/2008
EP   2617365 A2   7/2013
(Continued)

OTHER PUBLICATIONS

Extended European Search Report for application No. 19199644 dated Nov. 25, 2019.
(Continued)

*Primary Examiner* — Katrina M Stransky
*Assistant Examiner* — Brigid K Byrd
(74) *Attorney, Agent, or Firm* — Carter, DeLuca & Farrell, LLP

(57) ABSTRACT

A system for removal of a tissue specimen from an internal body cavity includes a cannula arrangement having an access cannula including a first elongated tubular member, a deployment cannula including a second elongated tubular member configured for insertion into the first lumen, a deployment plunger including a proximal base and a plurality of engagement arms extending distally from the proximal base, and an inner cannula including a third elongated tubular member. The system further includes a containment bag selectively deployable from the cannula arrangement. Distal advancement of the deployment cannula relative to the access cannula deploys a first portion of the containment bag from the cannula arrangement, and distal advancement of the deployment plunger relative to the deployment cannula and the access cannula deploys a second portion of the containment bag from the cannula arrangement.

6 Claims, 17 Drawing Sheets

(52) U.S. Cl.
CPC ...... *A61B 17/3421* (2013.01); *A61B 17/3423* (2013.01); *A61B 17/0469* (2013.01); *A61B 17/29* (2013.01); *A61B 90/361* (2016.02); *A61B 2017/00278* (2013.01); *A61B 2017/00287* (2013.01); *A61B 2017/00367* (2013.01); *A61B 2017/00867* (2013.01); *A61B 2017/320024* (2013.01); *A61B 2017/4216* (2013.01); *A61B 2018/1407* (2013.01)

(56) References Cited

U.S. PATENT DOCUMENTS

| | | | |
|---|---|---|---|
| 5,643,283 | A | 7/1997 | Younker |
| 6,059,793 | A | 5/2000 | Pagedas |
| 6,156,055 | A | 12/2000 | Ravenscroft |
| 6,162,209 | A | 12/2000 | Gobron et al. |
| 6,171,317 | B1 | 1/2001 | Jackson et al. |
| 6,206,889 | B1 | 3/2001 | Bennardo |
| 6,224,612 | B1 | 5/2001 | Bates et al. |
| 6,228,095 | B1 | 5/2001 | Dennis |
| 6,248,113 | B1 | 6/2001 | Fina |
| 6,258,102 | B1 | 7/2001 | Pagedas |
| 6,264,663 | B1 | 7/2001 | Cano |
| 6,270,505 | B1 | 8/2001 | Yoshida et al. |
| 6,280,451 | B1 | 8/2001 | Bates et al. |
| 6,344,026 | B1 | 2/2002 | Burbank et al. |
| 6,350,266 | B1 | 2/2002 | White et al. |
| 6,350,267 | B1 | 2/2002 | Stefanchik |
| 6,358,198 | B1 | 3/2002 | Levin et al. |
| 6,368,328 | B1 | 4/2002 | Chu et al. |
| 6,383,195 | B1 | 5/2002 | Richard |
| 6,383,197 | B1 | 5/2002 | Conlon et al. |
| 6,387,102 | B2 | 5/2002 | Pagedas |
| 6,406,440 | B1 | 6/2002 | Stefanchik |
| 6,409,733 | B1 | 6/2002 | Conlon et al. |
| 6,447,523 | B1 | 9/2002 | Middleman et al. |
| 6,530,923 | B1 | 3/2003 | Dubrul et al. |
| 6,537,273 | B1 | 3/2003 | Sosiak et al. |
| 6,752,822 | B2 | 6/2004 | Jespersen |
| 6,805,699 | B2 | 10/2004 | Shimm |
| 6,951,533 | B2 | 10/2005 | Foley |
| 6,986,774 | B2 | 1/2006 | Middleman et al. |
| 7,037,275 | B1 | 5/2006 | Marshall et al. |
| 7,052,501 | B2 | 5/2006 | McGuckin, Jr. |
| 7,087,062 | B2 | 8/2006 | Dhindsa |
| 7,101,379 | B2 | 9/2006 | Gregory, Jr. et al. |
| 7,101,380 | B2 | 9/2006 | Khachin et al. |
| 7,112,172 | B2 | 9/2006 | Orban, III et al. |
| 7,115,125 | B2 | 10/2006 | Nakao et al. |
| 7,144,400 | B2 | 12/2006 | Byrum et al. |
| 7,169,154 | B1 | 1/2007 | Que et al. |
| 7,229,418 | B2 | 6/2007 | Burbank et al. |
| 7,285,126 | B2 | 10/2007 | Sepetka et al. |
| 7,316,692 | B2 | 1/2008 | Huffmaster |
| 7,357,801 | B2 | 4/2008 | Burbank et al. |
| 7,534,252 | B2 | 5/2009 | Sepetka et al. |
| 7,547,310 | B2 | 6/2009 | Whitfield |
| 7,615,013 | B2 | 11/2009 | Clifford et al. |
| 7,618,437 | B2 | 11/2009 | Nakao |
| 7,645,283 | B2 | 1/2010 | Reynolds et al. |
| 7,670,346 | B2 | 3/2010 | Whitfield |
| 7,678,118 | B2 | 3/2010 | Bates et al. |
| 7,722,626 | B2 | 5/2010 | Middleman et al. |
| 7,727,227 | B2 | 6/2010 | Teague et al. |
| 7,731,722 | B2 | 6/2010 | Lavelle et al. |
| 7,731,723 | B2 | 6/2010 | Kear et al. |
| 7,762,959 | B2 | 7/2010 | Bilsbury |
| 7,762,960 | B2 | 7/2010 | Timberlake et al. |
| 7,875,038 | B2 | 1/2011 | Que et al. |
| 7,892,242 | B2 | 2/2011 | Goldstein |
| 7,914,540 | B2 | 3/2011 | Schwartz et al. |
| 7,918,860 | B2 | 4/2011 | Leslie et al. |
| 7,955,292 | B2 | 6/2011 | Leroy et al. |
| 8,057,485 | B2 | 11/2011 | Hollis et al. |
| 8,075,567 | B2 | 12/2011 | Taylor et al. |
| 8,118,816 | B2 | 2/2012 | Teague |
| 8,152,820 | B2 | 4/2012 | Mohamed et al. |
| 8,172,772 | B2 | 5/2012 | Zwolinski et al. |
| 8,211,115 | B2 | 7/2012 | Cheng et al. |
| 8,282,572 | B2 | 10/2012 | Bilsbury |
| 8,337,510 | B2 | 12/2012 | Rieber et al. |
| 8,348,827 | B2 | 1/2013 | Zwolinski |
| 8,409,216 | B2 | 4/2013 | Parihar et al. |
| 8,414,596 | B2 | 4/2013 | Parihar et al. |
| 8,419,749 | B2 | 4/2013 | Shelton, IV et al. |
| 8,425,533 | B2 | 4/2013 | Parihar et al. |
| 8,430,826 | B2 | 4/2013 | Uznanski et al. |
| 8,435,237 | B2 | 5/2013 | Bahney |
| 8,444,655 | B2 | 5/2013 | Parihar et al. |
| 8,486,087 | B2 | 7/2013 | Fleming |
| 8,512,351 | B2 | 8/2013 | Teague |
| 8,579,914 | B2 | 11/2013 | Menn et al. |
| 8,585,712 | B2 | 11/2013 | O'Prey et al. |
| 8,591,521 | B2 | 11/2013 | Cherry et al. |
| 8,652,147 | B2 | 2/2014 | Hart |
| 8,721,658 | B2 | 5/2014 | Kahle et al. |
| 8,734,464 | B2 | 5/2014 | Grover et al. |
| 8,777,961 | B2 | 7/2014 | Cabrera et al. |
| 8,795,291 | B2 | 8/2014 | Davis et al. |
| 8,821,377 | B2 | 9/2014 | Collins |
| 8,827,968 | B2 | 9/2014 | Taylor et al. |
| 8,870,894 | B2 | 10/2014 | Taylor et al. |
| 8,906,035 | B2 | 12/2014 | Zwolinski et al. |
| 8,956,370 | B2 | 2/2015 | Taylor et al. |
| 8,968,329 | B2 | 3/2015 | Cabrera |
| 8,986,321 | B2 | 3/2015 | Parihar et al. |
| 9,005,215 | B2 | 4/2015 | Grover et al. |
| 9,017,328 | B2 | 4/2015 | Bahney |
| 9,017,340 | B2 | 4/2015 | Davis |
| 9,033,995 | B2 | 5/2015 | Taylor et al. |
| 9,084,588 | B2 | 7/2015 | Farascioni |
| 9,101,342 | B2 | 8/2015 | Saleh |
| 9,113,848 | B2 | 8/2015 | Fleming et al. |
| 9,113,849 | B2 | 8/2015 | Davis |
| 9,308,008 | B2 | 4/2016 | Duncan et al. |
| 9,364,201 | B2 | 6/2016 | Orban, III |
| 9,364,202 | B2 | 6/2016 | Menn et al. |
| 9,370,341 | B2 | 6/2016 | Ceniccola et al. |
| 9,370,378 | B2 | 6/2016 | O'Prey et al. |
| 9,375,224 | B2 | 6/2016 | Jansen |
| 9,414,817 | B2 | 8/2016 | Taylor et al. |
| 9,468,452 | B2 | 10/2016 | Menn et al. |
| 9,486,188 | B2 | 11/2016 | Secrest et al. |
| 9,522,034 | B2 | 12/2016 | Johnson et al. |
| 9,549,747 | B2 | 1/2017 | Carlson |
| 9,579,115 | B2 | 2/2017 | Kahle et al. |
| 9,592,067 | B2 | 3/2017 | Hartoumbekis |
| 9,622,730 | B2 | 4/2017 | Farascioni |
| 9,629,618 | B2 | 4/2017 | Davis et al. |
| 9,642,638 | B1 | 5/2017 | Carrier |
| 9,655,644 | B2 | 5/2017 | Collins |
| 9,730,716 | B2 | 8/2017 | Secrest et al. |
| 9,789,268 | B2 | 10/2017 | Hart et al. |
| 9,808,228 | B2 | 11/2017 | Kondrup et al. |
| 9,826,997 | B2 | 11/2017 | Cherry et al. |
| 9,867,600 | B2 | 1/2018 | Parihar et al. |
| 9,877,893 | B2 | 1/2018 | Taylor et al. |
| 2006/0200170 | A1 | 9/2006 | Aranyi |

FOREIGN PATENT DOCUMENTS

| | | |
|---|---|---|
| WO | 20040002334 A1 | 1/2004 |
| WO | 2014134285 A1 | 9/2014 |
| WO | 2014/158880 A1 | 10/2014 |

OTHER PUBLICATIONS

Extended European Search Report issued in corresponding EP application No. 18152263.2 dated Feb. 23, 2018, 7 pages.

* cited by examiner

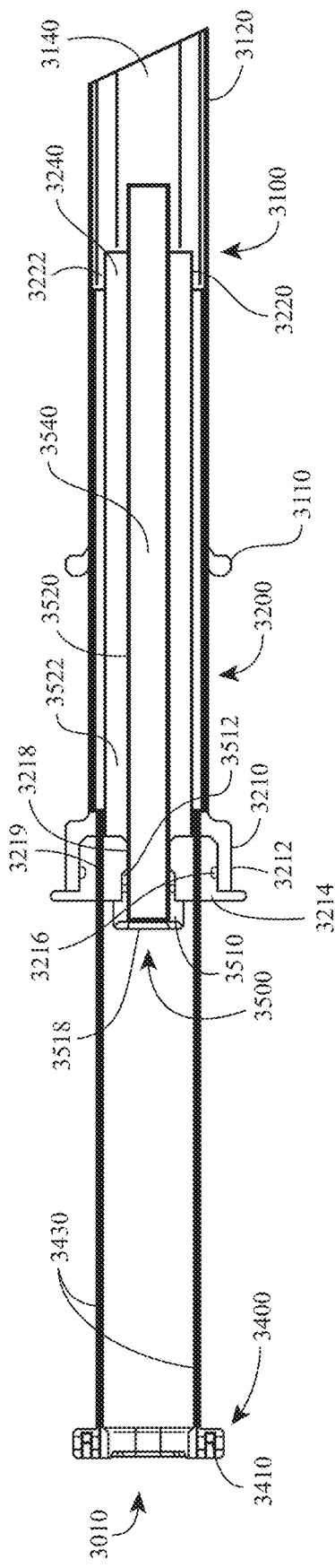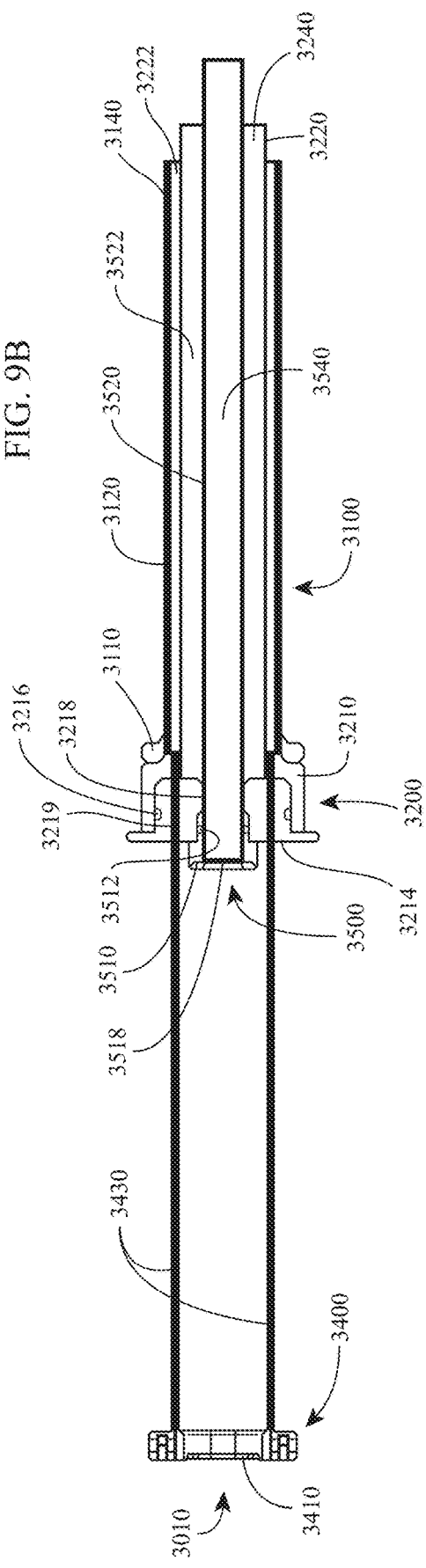

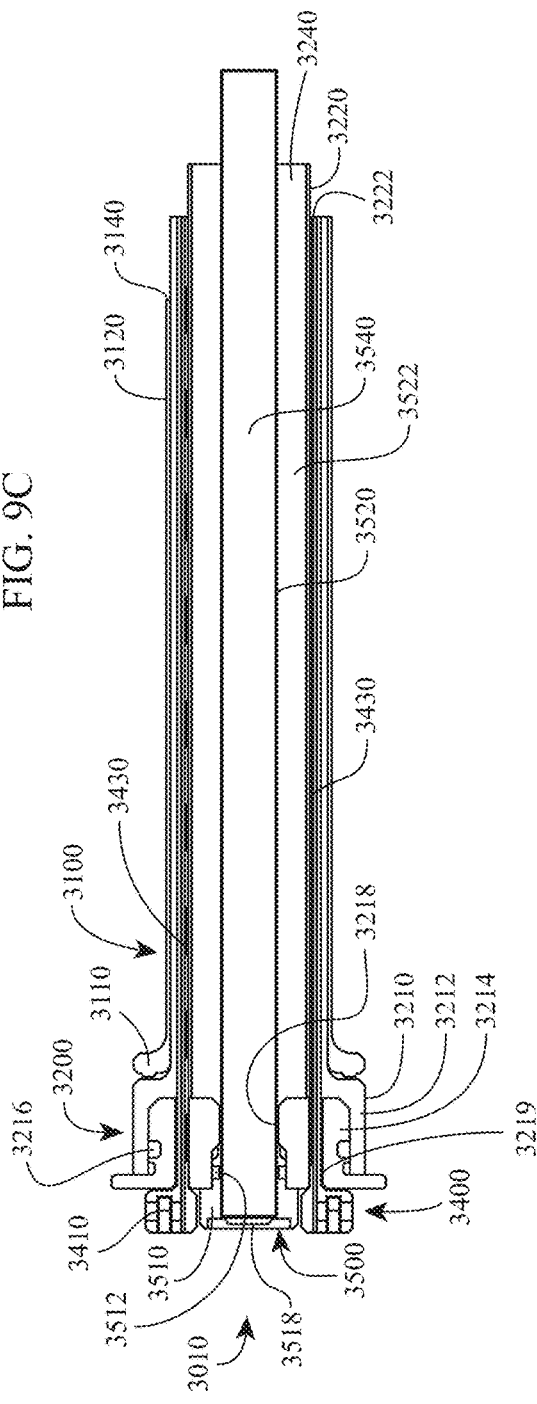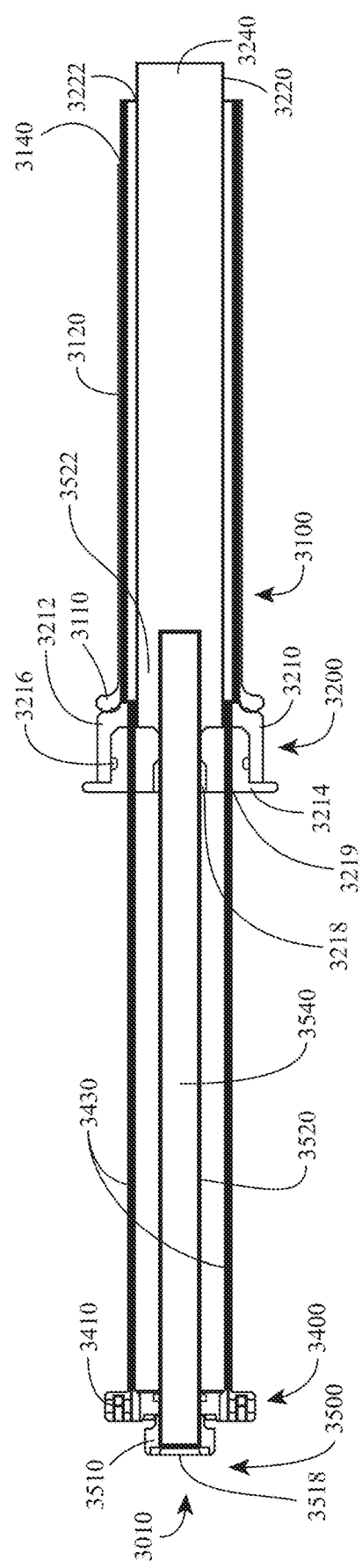

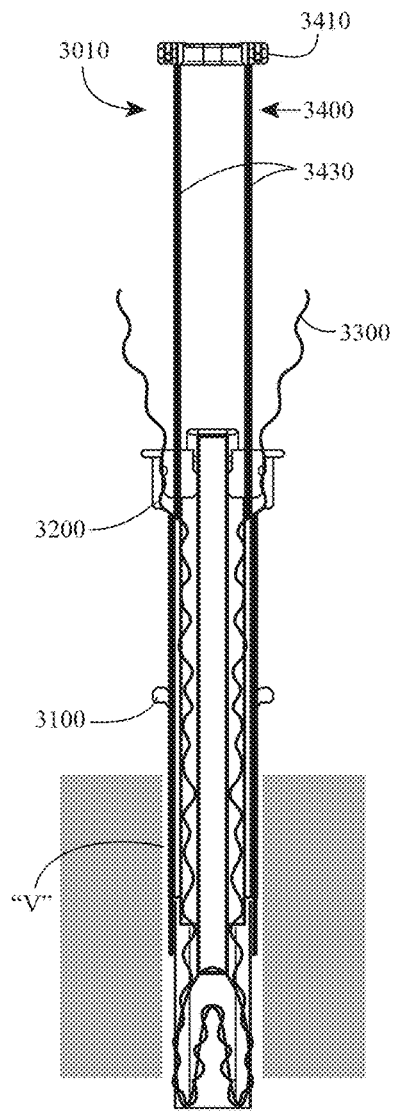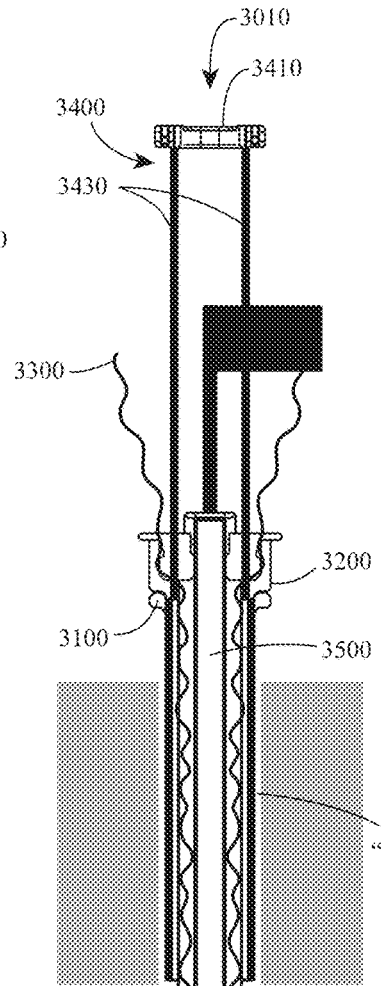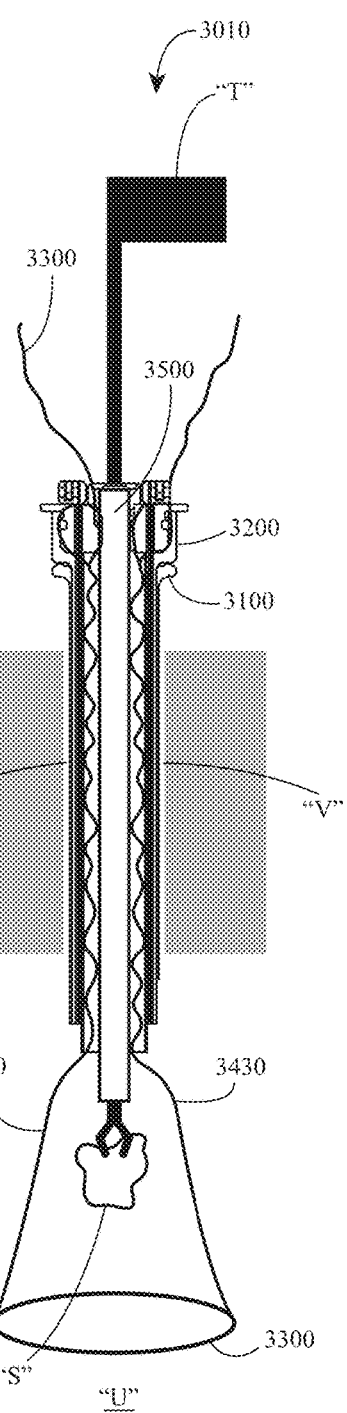

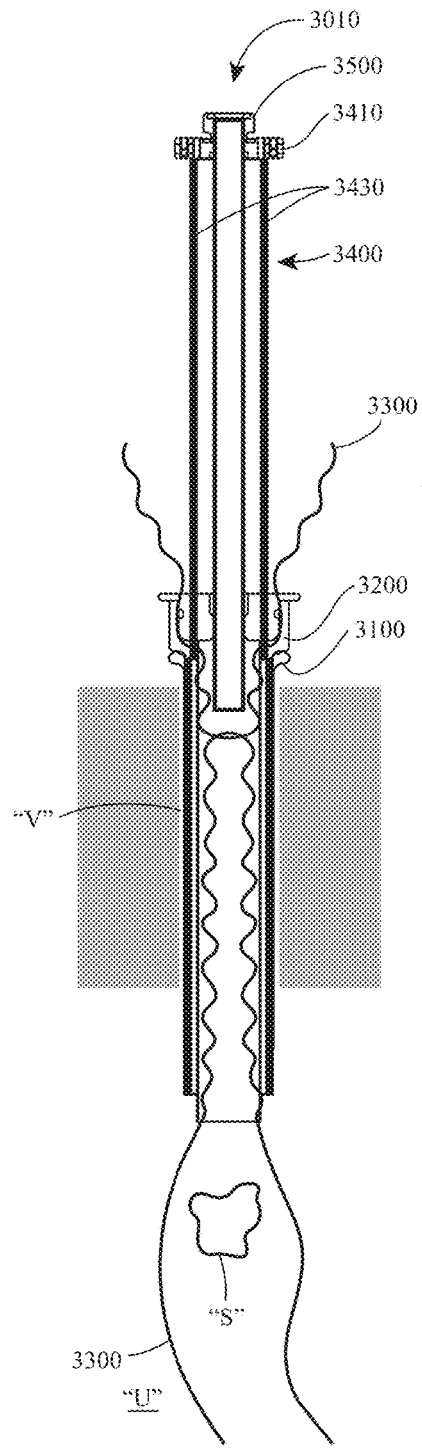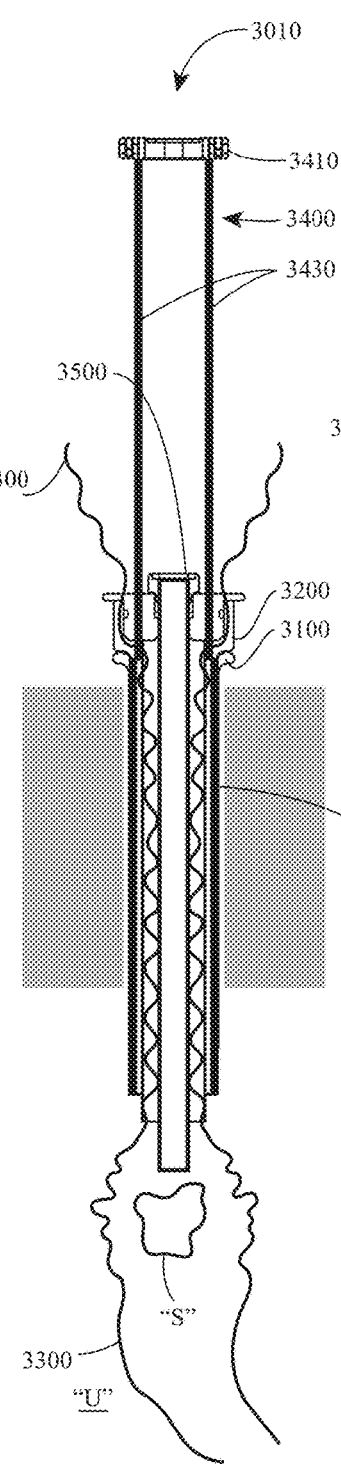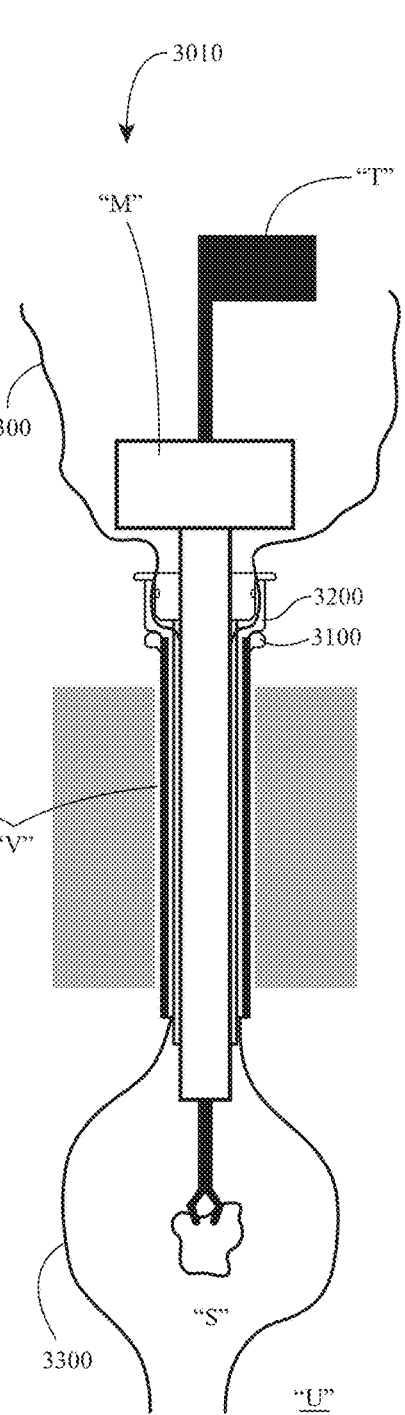

DEVICES, SYSTEMS, AND METHODS FOR LARGE TISSUE SPECIMEN REMOVAL

CROSS-REFERENCE TO RELATED APPLICATIONS

This application claims the benefit of U.S. Provisional Patent Application No. 62/448,266, filed on Jan. 19, 2017; U.S. Provisional Patent Application No. 62/461,488, filed on Feb. 21, 2017; and U.S. Provisional Patent Application No. 62/515,622, filed on Jun. 6, 2017. The entire contents of each of these applications is hereby incorporated herein by reference.

BACKGROUND

Technical Field

The present disclosure relates to tissue specimen removal and, more particularly, to devices, systems, and methods facilitating removal of a large tissue specimen from an internal body cavity, e.g., pelvic cavity.

Background of Related Art

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity.

During such minimally-invasive surgical procedures, it is common that a cyst, tumor, or other affected tissue is required to be removed. In these and other procedures where cancerous tissue is required to be removed, removal of the tissue specimen(s) in an enclosed environment is highly desirable to inhibit seeding of cancer cells. Thus, with respect to breaking down large tissue specimens for removal through minimally-invasive openings, there is the added challenge of doing so within an enclosed environment.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a system for removal of a tissue specimen from an internal body cavity. The system includes an access cannula, a deployment cannula, and a containment bag. The access cannula includes a first elongated tubular member and defines a lumen extending through the first elongated tubular member. The deployment cannula includes a second elongated tubular member and a plurality of engagement arms engaged to the second elongated tubular member at fixed ends thereof and extending to free ends thereof. The deployment cannula is configured for slidable positioning within the access cannula and is movable relative there to between an initial condition, wherein the engagement arms are disposed within the lumen of the access cannula and are retained in position adjacent the second elongated tubular member, and a deployed condition, wherein the engagement arms are disposed distally of the lumen and extend radially outwardly from the second elongated tubular member. The containment bag includes a plurality of pockets, each pocket configured to receive one of the engagement arms of the deployment cannula. In the initial condition, a distal end portion of the containment bag is disposed within the lumen of the access cannula between the first and second elongated tubular members. In the deployed condition, the distal end portion of the containment bag is urged distally from the access cannula by the engagement arms and biased towards an open configuration by the engagement arms to present a mouth for receipt of a tissue specimen and/or to urge the mouth about the tissue specimen.

In an aspect of the present disclosure, the access cannula includes a proximal hub disposed at a proximal end of the first elongated tubular member. In such aspects, the lumen extends through the proximal hub.

In another aspect of the present disclosure, the first elongated tubular member defines a beveled distal end.

In another aspect of the present disclosure, the deployment cannula includes a proximal hub disposed at a proximal end of the second elongated tubular member.

In yet another aspect of the present disclosure, the deployment cannula defines a second lumen extending through the second elongated tubular member.

In still another aspect of the present disclosure, the deployment cannula is configured as a morcellator.

In another aspect of the present disclosure, the containment bag includes a reinforced rim at the distal end portion thereof. The reinforced rim may be resiliently flexible, maintained against its bias in the initial condition, and returned under bias in the deployed condition.

In yet another aspect of the present disclosure, the containment bag further includes a body portion and a proximal end portion. The body portion is disposed between the proximal and distal end portions.

In still another aspect of the present disclosure, the containment bag includes a grasping tab extending from the distal end portion thereof. The distal end portion of the containment bag may be beveled with the grasping tab extending from a protruding portion of the beveled distal end portion. Additionally or alternatively, the grasping tab may define an aperture therethrough.

In another aspect of the present disclosure, the containment bag includes a suture arrangement extending from the distal end portion thereof. The suture arrangement, in aspects, may include a plurality of sutures. The first ends of the sutures may be spaced-apart about and attached to the distal end portion of the containment bag. Additionally or alternatively, the second ends of the sutures may be attached to one another.

In yet another aspect of the present disclosure, the system further includes a second access cannula configured to receive a grasper therethrough to facilitate positioning of a tissue specimen within the containment bag.

In still yet another aspect of the present disclosure, the system includes a third access cannula configured to receive a surgical camera therethrough to provide visualization within an internal body cavity.

A method of removing a tissue specimen from an internal body cavity provided in accordance with the present disclosure includes inserting an access cannula through a vagina and into a pelvic cavity, deploying a first end portion of a containment bag from the access cannula into the pelvic cavity while a second end portion of the containment bag remains external of the pelvic cavity or within the access cannula, positioning a tissue specimen within the containment bag through the first end portion of the containment bag, withdrawing the first end portion of the containment bag through an abdominal opening, morcellating the tissue specimen, tying off the second end portion of the containment bag, and withdrawing the containment bag through the abdominal opening such that the second end portion of the containment bag enters the pelvic cavity via the vagina and exits the pelvic cavity through the abdominal opening. The containment bag may alternatively be removed through the vagina in the opposite fashion.

In an aspect of the present disclosure, deploying the first end portion of the containment bag includes advancing a deployment cannula through the access cannula to urge the first end portion of the containment bag into the pelvic cavity.

In another aspect of the present disclosure, the deployment cannula includes a plurality of engagement arms. The engagement arms are biased outwardly from an elongated tubular member of the deployment cannula such that, upon advancing the deployment cannula through the access cannula, the engagement arms are outwardly expanded under bias to outwardly expand the first end portion of the containment bag within the pelvic cavity.

In still another aspect of the present disclosure, the method further includes visualizing at least one of inserting, deploying, positioning, withdrawing, or morcellating through use of a surgical camera inserted through another abdominal opening. The another abdominal opening provides triangulation with the vagina and the abdominal opening.

In another aspect of the present disclosure, morcellating the tissue specimen includes pulling an RF loop through the tissue specimen to cut the tissue specimen into smaller strips. A grasper may be used to grasp the tissue specimen to maintain the tissue specimen in position during morcellation of the tissue specimen.

In yet another aspect of the present disclosure, positioning the tissue specimen within the containment bag includes inserting a tenaculum through the access cannula and the containment bag, grasping the tissue specimen, and pulling the tissue specimen through the first end portion of the containment bag into the containment bag and/or advancing the containment bag in the opposite direction pushing the containment bag about the tissue specimen.

In another aspect, a second stage deployment of the containment bag may be effected where the tissue specimen is located and where morcellation will occur. This can be done by further advancing the containment bag via engagement arms and/or a tube inserted through the access cannula forcing the containment bag further therefrom.

In yet another aspect, a line mid-way on the containment bag may be provided to indicate how far to pull the containment bag out of the abdominal opening in order to position it ideally with the least amount of pleating for maximized visualization.

In still yet another aspect of the present disclosure, withdrawing the first end portion of the containment bag through the abdominal opening includes inserting a grasper through the abdominal opening, gasping a tab at the first end portion of the containment bag, and pulling the first end portion of the containment bag out through the abdominal opening. As an alternative to a tab, a pull-string and loop may be disposed about the first end portion of the tab for similar purposes.

Another system for removal of a tissue specimen from an internal body cavity provided in accordance with aspects of the present disclosure includes a cannula arrangement and a containment bag. The cannula arrangement includes an access cannula, a deployment cannula, a deployment plunger, and an inner cannula. The access cannula includes a first elongated tubular member defining a first lumen extending therethrough. The deployment cannula includes a second elongated tubular member defining a second lumen extending therethrough and is configured for insertion into the first lumen. The second elongated tubular member defines a diameter less than a diameter of the first elongate tubular member such that a first annular spacing is defined between the first and second elongated tubular members when the second elongated tubular member is inserted into the first lumen. The deployment plunger includes a proximal base and a plurality of engagement arms extending distally from the proximal base. The plurality of engagement arms are configured for insertion through the first annular space. The inner cannula includes a third elongated tubular member defining a third lumen extending therethrough and is configured for insertion into the second lumen. The third elongated tubular member defines a diameter less than a diameter of the second elongate tubular member such that a second annular spacing is defined between the second and third elongated tubular members when the third elongated tubular member is inserted into the second lumen. The containment bag is selectively deployable from the cannula arrangement, whereby: distal advancement of the deployment cannula relative to the access cannula deploys a first portion of the containment bag from the cannula arrangement; and distal advancement of the deployment plunger relative to the deployment cannula and the access cannula deploys a second portion of the containment bag from the cannula arrangement.

In an aspect of the present disclosure, the first portion of the containment bag is disposed within the first lumen.

In another aspect of the present disclosure, the second portion of the containment bag is disposed within the first annular space.

In another aspect of the present disclosure, proximal withdrawal and subsequent distal advancement of the inner cannula relative to the deployment cannula and the access cannula deploys a third portion of the containment bag from the cannula arrangement. In such aspects, the third portion of the containment bag may be disposed within the second annular space.

In still another aspect of the present disclosure, distal advancement of the deployment plunger relative to the deployment cannula and the access cannula urges a portion of each of the engagement fingers distally from the deployment cannula and the access cannula. In such aspects, the engagement fingers may be biased towards a radially-outwardly extending configuration such that, upon extension thereof distally from the deployment cannula and the access cannula, the engagement fingers extend radially-outwardly. Alternatively or additionally, distal end portions of the engagement fingers may be configured for receipt within pockets defined within the containment bag.

In yet another aspect of the present disclosure, the deployment cannula further includes a proximal hub defining a central opening communicating with the second lumen and a plurality of channels radially-spaced from the central opening and configured to receive the plurality of engagement arms therethrough. The proximal hub of the deployment cannula may include a base portion and an insert portion releasably engagable with the base portion. Different insert portions may be interchangeable with the insert portion.

A method of containing a tissue specimen disposed within an internal body cavity provided in accordance with the present disclosure includes inserting a cannula arrangement through a vagina and into a pelvic cavity. The cannula arrangement includes an access cannula, a deployment cannula slidably disposed within the access cannula, a deployment plunger having a plurality of engagement arms slidably disposed within a first annular space defined between the access cannula and the deployment cannula, and an inner cannula slidably disposed within the deployment cannula. A containment bag is disposed within the cannula arrangement.

The method further includes distally advancing the deployment cannula relative to the access cannula to deploy a first portion of the containment bag from the cannula arrangement, in the pelvic cavity, and at least partially about a tissue specimen, and distally advancing the deployment plunger relative to the deployment cannula and the access cannula to deploy a second portion of the containment bag from the cannula arrangement and into the pelvic cavity such that the containment bag is further disposed about the tissue specimen.

In aspects, the method further includes proximally withdrawing the inner cannula from the deployment cannula and reinserting the inner cannula distally through the deployment cannula to deploy a third portion of the containment bag from the cannula arrangement and into the pelvic cavity.

In aspects, the method further includes withdrawing the first portion of the containment bag from the pelvic cavity through an abdominal port.

In aspects, the method further includes inserting a tenaculum or a grasper through the inner cannula and grasping the specimen with the tenaculum or grasper to maintain the specimen in position or pull the specimen proximally during deployment of the first and/or second portions of the containment bag.

In aspects, the method further includes proximally withdrawing the inner cannula and inserting a morcellator through the deployment cannula and into the pelvic cavity within the containment bag. In such aspects, an insert portion of the deployment cannula is replaced with a different insert portion after proximally withdrawing the inner cannula and before inserting the morcellator.

Another system for removal of a tissue specimen from an internal body cavity includes an access cannula defining a lumen extending therethrough, a containment bag selectively deployable from the lumen of the access cannula and having an open distal end portion, and a suture arrangement extending from the open distal end portion of the containment bag.

The suture arrangement may include a plurality of sutures arranged such that first ends of the sutures are spaced-apart about and attached to the distal end portion of the containment bag. The second ends of the sutures are attached to one another.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements and:

FIGS. 9A-9F are longitudinal, cross-sectional views of another tissue specimen removal system provided in accordance with the present disclosure, illustrating the various positions thereof;

FIGS. 10A-10F illustrate use of the tissue specimen removal system of FIGS. 9A-9F for deploying a containment bag about a large tissue specimen within an internal body cavity, enclosing the large tissue specimen within the containment bag, and breaking down the large tissue specimen into smaller pieces to enable removal from the internal body cavity;

DETAILED DESCRIPTION

The present disclosure provides devices, systems, and methods facilitating removal of a large tissue specimen from an internal body cavity, e.g., pelvic cavity, while maintain the large tissue specimen in an enclosed environment during break down and removal from the internal body cavity.

Figure 1:
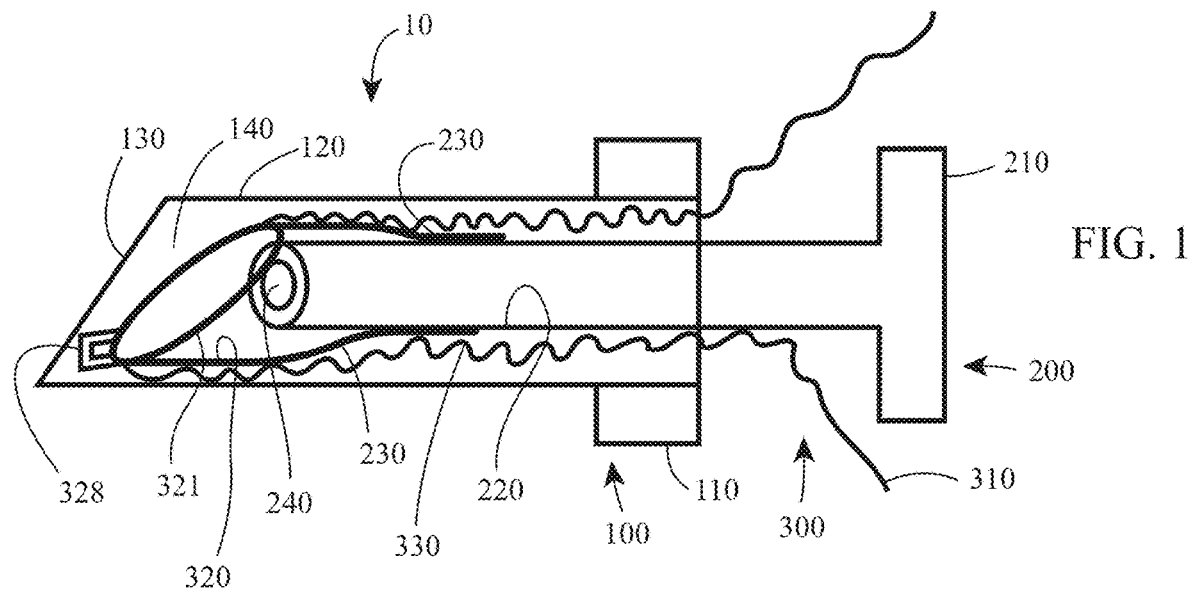
FIG. 1 is a side, longitudinal, cross-sectional view of a tissue specimen removal system provided in accordance with the present disclosure, disposed in an initial condition.
Figure 2:
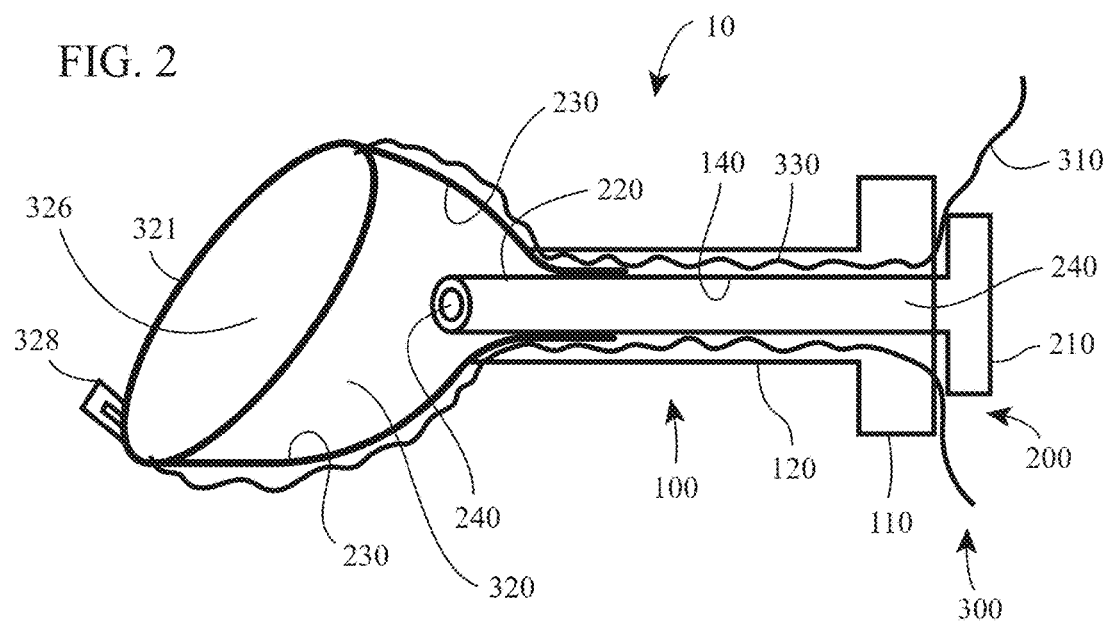
FIG. 2 is a side, longitudinal, cross-sectional view of the tissue specimen removal system of FIG. 1, disposed in a deployed condition.
Figure 3:
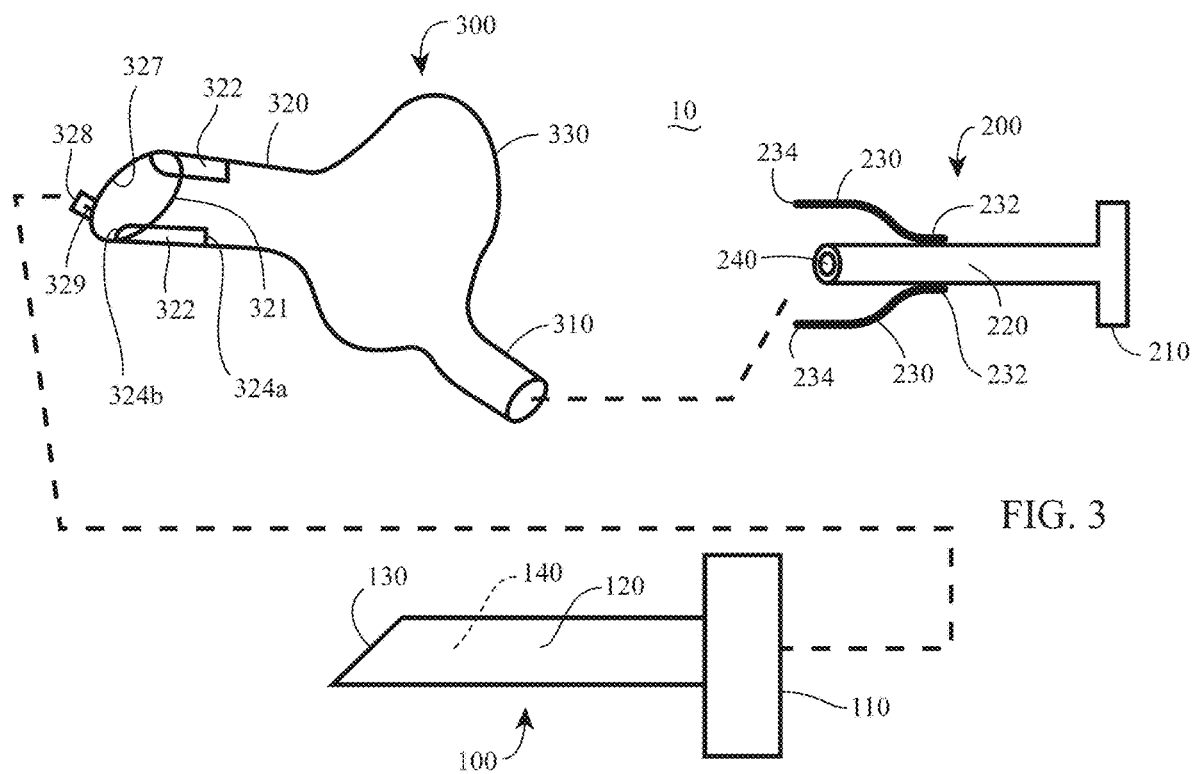
FIG. 3 is an exploded view of the tissue specimen removal system of FIG. 1.

Turning to FIGS. 1-3, a system 10 provided in accordance with the present disclosure generally includes an access cannula 100, a deployment cannula 200, and a containment bag 300. Access cannula 100 includes a proximal hub 110, an elongated tubular sleeve 120, and a beveled distal end portion 130. A lumen 140 extends through proximal hub 110 and elongated tubular sleeve 120 to enable the insertion of deployment cannula 200, containment bag 300, and, in some embodiments, other surgical instruments, through access cannula 100 and into the internal body cavity.

Proximal hub 110 of access cannula 100 is configured to remain externally-disposed and may include an insufflation port (not shown) to enable the introduction of insufflation fluid through lumen 140 and into the internal body cavity to insufflate the internal body cavity. To this end, proximal hub 110 may further include one or more seals (not shown) configured to seal lumen 140 in the absence of deployment cannula 200, containment bag 300, and/or other surgical instruments inserted therethrough, and/or to establish a seal about deployment cannula 200, containment bag 300, and/or other surgical instruments inserted through lumen 140, in order to maintain the internal body cavity in an insufflated condition.

Elongated tubular sleeve 120 of access cannula 100 is configured to extend through an access opening an into the internal body cavity such that beveled distal end portion 130 is at least partially disposed within the internal body cavity, while proximal hub 110 remains externally disposed. For example, elongated tubular sleeve 120 may be configured to extend through the vagina into the pelvic cavity or, if the cervix is still intact, through the vagina and an incision in the posterior vaginal fornix into the pelvic cavity. Beveled distal end portion 130 of access cannula 100 is configured to facilitate atraumatic insertion of elongated tubular sleeve 120 through an access opening and into the internal body cavity, although configurations other than beveled are also contemplated.

Continuing with reference to FIGS. 1-3 deployment cannula 200 includes a proximal hub 210, an elongated tubular sleeve 220, and a plurality of engagement fingers 230. A lumen 240 extends through proximal hub 210 and elongated tubular sleeve 220 to enable the insertion of surgical instruments through deployment cannula 200 and into the internal body cavity. Deployment cannula 200 is configured for slidable positioning within lumen 140 of access cannula 100 and may be positioned therein in an initial condition (FIG. 1) during manufacturing or may be inserted into access cannula 100 by a user.

Proximal hub 210 of deployment cannula 200 is configured to remain externally-disposed relative to the internal surgical site and access cannula 100. More specifically, in an initial condition (FIG. 1) of system 10, proximal hub 210 is proximally-spaced from proximal hub 110 of access cannula 100. In a deployed condition (FIG. 2), on the other hand, proximal hub 210 is positioned proximally adjacent proximal hub 110. Similarly as with proximal hub 110 of access cannula 100, proximal hub 210 of deployment cannula 200 may include one or more seals (not shown) configured to seal lumen 240 in the absence of surgical instruments inserted therethrough and/or to establish a seal about surgical instruments inserted through lumen 140, in order to maintain the internal body cavity in an insufflated condition. Proximal hub 210 of deployment cannula 200 may also include an insufflation port (not shown) to enable the introduction of insufflation fluid through lumen 240 to, for example, insufflate containment bag 300.

Elongated tubular sleeve 220 of deployment cannula 200 is configured to extend through lumen 140 of access cannula 100 and into the internal body cavity. More specifically, elongated tubular sleeve 220 defines a suitable length so as to enable proximal hub 210 of deployment cannula 200 to remain externally disposed of the internal body cavity and access cannula 100 while a distal end of elongated tubular sleeve 220 extends to or beyond beveled distal end portion 130 of access cannula 100. Further, elongated tubular sleeves 220 defines a suitable diameter relative to that of lumen 140 of access cannula 100 to enable positioning of elongated tubular sleeve 220 within lumen 140 of access cannula 100 with engagement fingers 230 and containment bag 300 disposed between elongated tubular sleeve 220 of deployment cannula 200 and elongated tubular sleeve 120 of access cannula 100.

Engagement fingers 230 are configured as cantilever springs each having a fixed end 232 and a free end 234. Although only two engagement fingers 230 are illustrated in the drawings, any suitable number of engagement fingers 230 may be provided. Engagement fingers 230 may be formed from a spring-metal, e.g., nitinol, or other suitable material, and are arranged radially-spaced about elongated tubular sleeve 220. More specifically, engagement fingers 230 are fixed to the exterior surface of elongated tubular sleeve 220 at the fixed ends 232 thereof and extend distally to free ends 234 thereof. Free ends 234 of engagement fingers 230 extend distally beyond the distal end of elongated tubular sleeve 220 and are biased radially-outwardly from elongated tubular sleeve 220 in the at-rest positions of engagement fingers 230. In the initial condition of system 10 (see FIG. 1), wherein elongated tubular sleeve 220 of deployment cannula 200 is disposed within lumen 140 of access cannula 100, engagement fingers 230 are retained, against their bias, in a contracted configuration, wherein engagement fingers 230 extend alongside the exterior of elongated tubular sleeve 220, thus enabling engagement fingers 230 and elongated tubular sleeve 220 to fit within lumen 140 of access cannula 100. Once deployment cannula 200 is advanced distally relative to access cannula 100 to the deployed condition (FIG. 2) of system 10, engagement fingers 230 extend distally from beveled distal end portion 130 of access cannula 100, thus enabling engagement fingers 230 to return under bias towards their at-rest position, wherein free ends 234 of engagement fingers 230 are radially-outwardly spaced from elongated tubular sleeve 220.

As an alternative to providing deployment cannula 200 with engagement fingers 230, engagement fingers 230 may be disposed on another surgical instrument to be used within the internal body cavity such as, for example, a morcellator (not shown). An exemplary morcellator for this purpose is described in Patent Application Publication No. US 2015/0073429, filed on Jun. 12, 2014, the entire contents of which are hereby incorporated herein by reference.

Figure 4:
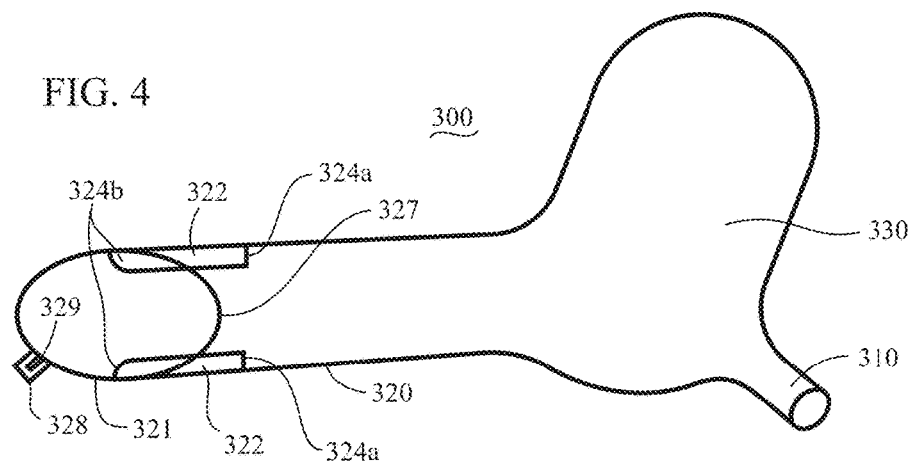
FIG. 4 is a perspective view of a containment bag of the tissue specimen removal system of FIG. 1.

Referring to FIGS. 3 and 4, containment bag 300 is configured for positioning, in the initial condition (FIG. 1) of system 10, in the annular space defined between elongated tubular sleeve 120 of access cannula 100 and elongated tubular sleeve 220 of deployment cannula 200, although a portion of containment bag 300 may extend proximally from both access cannula 100 and deployment cannula 200 in the initial condition (FIG. 1) of system 10. In the deployed condition (FIG. 2) of system 10, containment bag 300 is deployed into the internal body cavity under urging from deployment cannula 200 and is unfurled, thus presenting containment bag 300 to enable positioning of a tissue specimen(s) therein.

Containment bag 300 includes a first open end portion 310, a second open end portion 320, and a body portion 330 disposed between first and second open end portions 310, 320, respectively. First and second open end portions 310, 320, respectively, need not be disposed opposite one another but can be arranged relative to one another and body portion 330 so as to define any suitable configuration such as, for example, a dogleg, L-shape, C-shape, or other suitable configuration. The particular configuration of containment bag 300 may depend upon the desired access locations to be used during the tissue specimen removal procedure. Containment bag 300 may be formed from any suitable material. In particular, containment bag 300 may be formed from a transparent, tear-resistant, stretchable material to enable visualization into containment bag 300 from the exterior thereof, inhibit tearing, and facilitate manipulation of containment bag 300, tissue specimen(s), and/or surgical instrumentation during use.

First open end portion 310 of containment bag 300 defines a generally tubular, elongated configuration of sufficient length to enable first open end portion 310 to extend from the internal body cavity, through access cannula 100, to the exterior of the patient. This configuration separates the interior of containment bag 300 from surrounding patient tissue. First open end portion 310 of containment bag 300 may further include features (not shown) to facilitate sealed closure thereof such as, for example, a threaded lip configured to receive a screw-on cap, or may be configured to be sealed closed by way of a suture, clip, tying-off, or other suitable mechanism or method.

Second open end portion 320 of containment bag 300 likewise defines a generally tubular, elongated configuration. Second open end portion 320 defines a beveled end 321 and is of sufficient length to enable second open end portion 320 to extend from the internal body cavity, through a second access cannula 1100 (FIGS. 8A-8H), different from access cannula 100, to the exterior of the patient. Thus, first and second open end portions 310, 320 are capable of extending through access cannulas 100 (FIG. 1), 1100 (FIGS. 8A-8H), respectively, while body portion 330 of containment bag 300 is disposed within the internal body cavity. In addition or as an alternative to the features of first open end portion 310, second open end portion 320 may further include features (not shown) to facilitate sealed closure thereof such as, for example, a threaded lip configured to receive a screw-on cap, or may be configured to be sealed closed by way of a suture, clip, tying-off, or other suitable mechanism or method.

Figure 5:
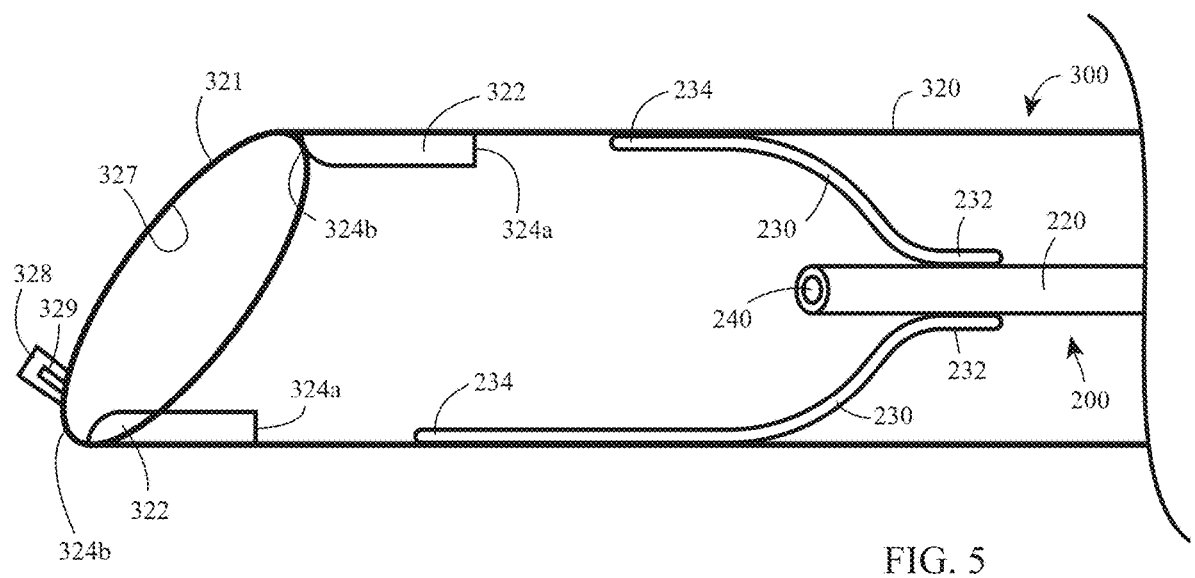
FIG. 5 is a side, perspective view of an end portion of the containment bag of FIG. 4 and a deployment cannula of the tissue specimen removal system of FIG. 1, illustrating the deployment cannula moving into engagement with the containment bag.
Figure 6:
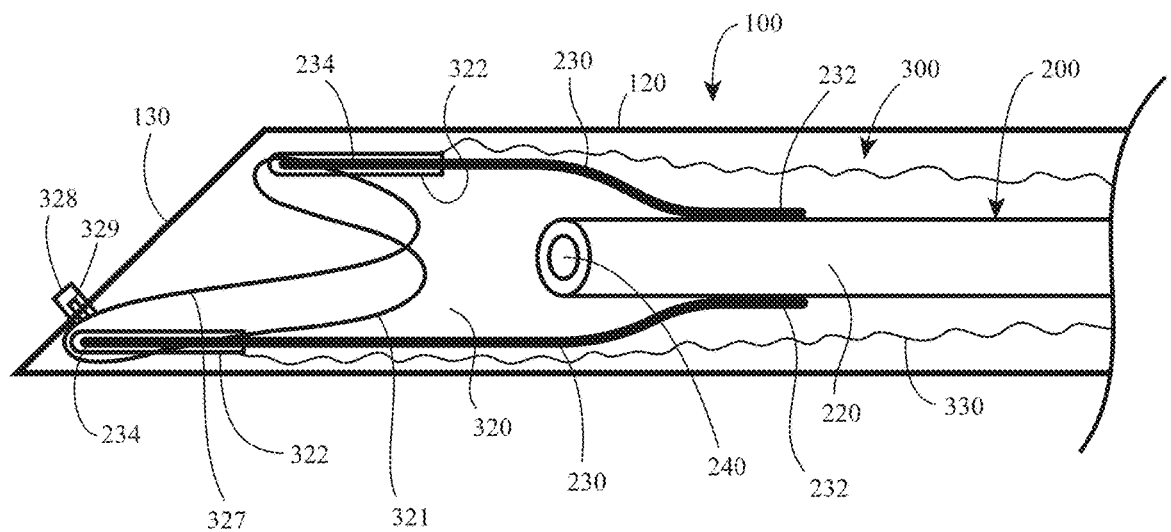
FIG. 6 is a side, cut-away view of the distal portion of the tissue specimen removal system of FIG. 1, illustrating the deployment cannula engaged with the containment bag within the access cannula in the initial condition of the system.

With additional reference to FIGS. 5 and 6, second open end portion 320 of containment bag 300 further includes a plurality of elongated pockets 322 disposed on an interior surface thereof. Elongated pockets 322 are arranged radially-spaced about the interior surface of second open end portion 320 of containment bag 300 and may correspond in number and position to the number and position of engagement fingers 230 of deployment cannula 200 (see FIG. 3). Each elongated pocket 322 defines a proximally-facing open end 324a configured to receive the free end 234 of one of the engagement fingers 230 of deployment cannula 200, and a closed, distally-facing end 234b. As such, engagement fingers 230 are configured to slide into elongated pockets 322 upon distal insertion of deployment cannula 200 into containment bag 300. As an alternative, engagement fingers 230 may be external to containment bag 320 and pockets 322 likewise disposed on the external side thereof.

In the initial condition (FIGS. 1 and 6) of system 10, deployment cannula 200 extends into containment bag 300 such that engagement fingers 230 are received within elongated pockets 322, with both deployment cannula 200 and containment bag 300 disposed within access cannula 100. In the deployed condition (FIG. 2) of system 10, the bias of engagement fingers 230 towards the radially-outwardly spaced position relative to elongated tubular sleeve 220 similarly expands second open end portion 320 of containment bag 300 providing a mouth 326 to facilitate passage of a tissue specimen into second open end portion 320 of containment bag 300.

Referring to FIGS. 3, 4, and 7A-7C, second open end portion 320 of containment bag 300 defines a reinforced rim 327 surrounding the opening thereof. Reinforced rim 327 may be formed from a spring-metal, e.g., nitinol, or other suitable material that is resiliently flexible, returning to a pre-determined shape in the absence of external forces applied thereto. This configuration allows reinforced rim 327 to be flexed or otherwise re-positioned to enable receipt of second open end portion 320 of containment bag 300 within lumen 140 of access cannula 100. Upon deployment from lumen 140 of access cannula 100, reinforced rim 327 returns to its at-rest configuration, thus maintaining mouth 326 in an open, expanded position to facilitate passage of a tissue specimen into second open end portion 320 of containment bag 300. First open end portion 310 of containment bag 300 may likewise define a reinforced rim (not shown) surrounding the opening thereof to facilitate maintaining the opening of first open end portion 310 in an open condition externally of the internal body cavity or, in embodiments, within the internal body cavity upon deployment from access cannula 100.

Figure 7A:
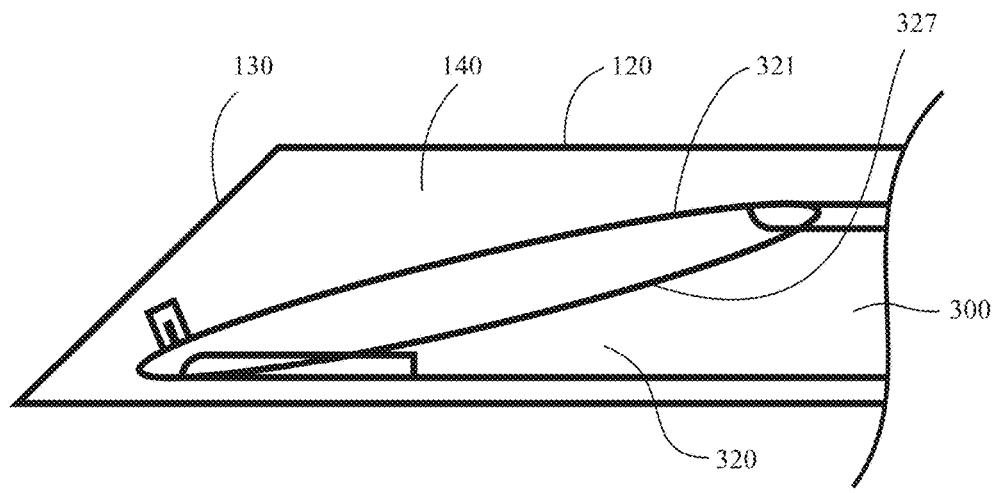
FIG. 7A is a side, cut-away view of a distal portion of the tissue specimen removal system of FIG. 1, illustrating one configuration of the containment bag collapsed within an access cannula of the tissue specimen removal system of FIG. 1 in the initial condition of the system.
Figure 7B:
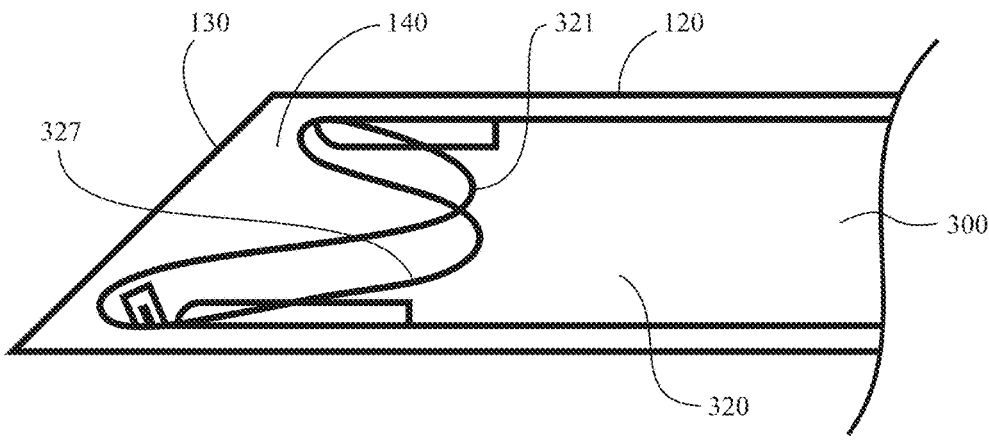
FIG. 7B is a side, cut-away view of the distal portion of the tissue specimen removal system of FIG. 1, illustrating another configuration of the containment bag collapsed within the access cannula in the initial condition of the system.
Figure 7C:
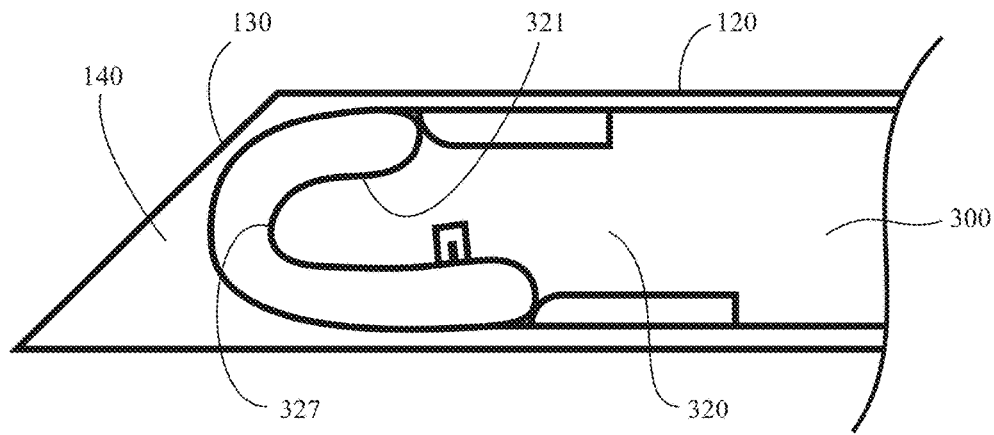
FIG. 7C is a side, cut-away view of the distal portion of the tissue specimen removal system of FIG. 1, illustrating another configuration of the containment bag collapsed within the access cannula in the initial condition of the system.

With reference to FIG. 7A, in embodiments, reinforced rim 327 may be manipulated to define an oval-shaped configuration and may be angled relative to lumen 140 of access cannula 100 to enable reinforced rim 327 to fit within lumen 140 of access cannula 100 in the initial condition of system 10 (FIG. 1). Alternatively, as illustrated in FIG. 7B, reinforced rim 327 may be manipulated to define an oval-shaped configuration and then bent to define a distally-facing C-shaped configuration to enable reinforced rim 327 to fit within lumen 140 of access cannula 100 in the initial condition of system 10 (FIG. 1). FIG. 7C illustrates another alternative, wherein reinforced rim 327 is manipulated to define an oval-shaped configuration and then bent to define a proximally-facing C-shaped configuration to enable reinforced rim 327 to fit within lumen 140 of access cannula 100 in the initial condition of system 10 (FIG. 1). Other suitable configurations are also contemplated.

Referring again to FIGS. 4-6, second open end portion 320 of containment bag 300 further includes a grasping tab 328 extending from beveled end 321 thereof. More specifically, grasping tab 328 extends from the further-extended side of beveled end 321 to facilitate grasping of tab 328. Tab 328 may further include an aperture 329 configured to receive a tooth, hook, or other suitable structure of a grasper "G" (FIG. 8D) to facilitate grasping of tab 328. As detailed below, the grasping of tab 328 enables manipulation of second open end portion 320 of containment bag 300 within the internal body cavity and/or withdrawal of second open end portion 320 from the internal body cavity.

With reference to FIG. 4, body portion 330 of containment bag 300 defines an enlarged diameter relative to first and second open end portions 310, 320, respectively, of containment bag 300 and is disposed therebetween. Body portion 330 is configured for positioning within the internal body cavity while either or both of first and second open end portions 310, 320, respectively, extend from the internal body cavity, through an access cannula 100, 1100 (FIGS. 8A-8H), to the exterior of the patient. Body portion 330 is configured to receive a tissue specimen to be removed and, with the tissue specimen disposed within body portion 330, enable breaking down, e.g., via morcellation, of the tissue specimen into smaller pieces to facilitate removal from the internal body cavity.

Turning to FIGS. 8A-8H, in conjunction with FIGS. 1-3, the use of system 10 in the removal of a large tissue specimen "S" from the pelvic cavity "U," maintaining the large tissue specimen "S" in an enclosed environment during break down and removal, is described. System 10 may be similarly used in the removal of other tissue specimen from other internal body cavities.

Figure 8A:
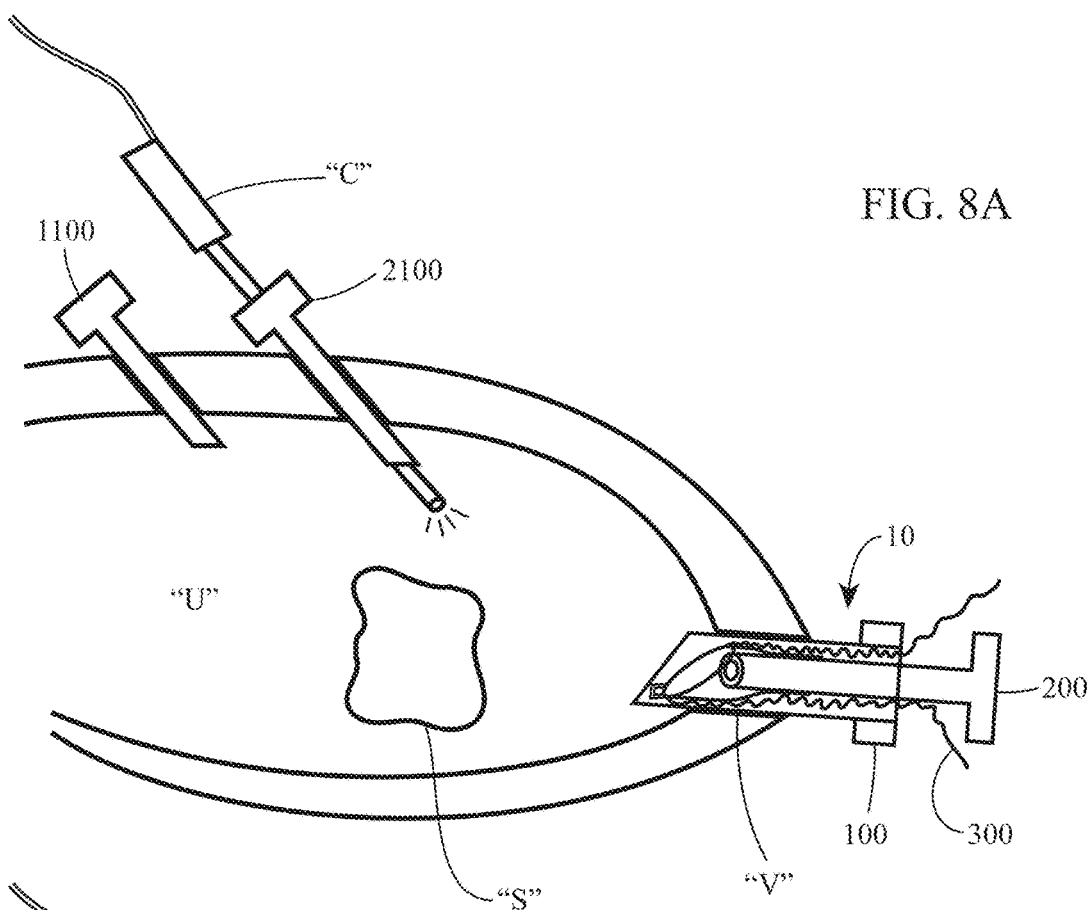
FIGS. 8A-8H illustrate use of the tissue specimen removal system of FIG. 1 for deploying the containment bag about a large tissue specimen within an internal body cavity, enclosing the large tissue specimen within the containment bag, breaking down the large tissue specimen into smaller pieces, and removing the contained pieces from the internal body cavity.

Referring initially to FIG. 8A, with system 10 disposed in the initial condition, access cannula 100, lead by beveled distal end 130 of elongated tubular sleeve 120, is advanced through the vagina "V" into the pelvic cavity "U" or, if the cervix is still intact, through the vagina "V" and an incision in the posterior vaginal fornix into the pelvic cavity "U." In the initial condition of access cannula 100, first open end portion 310 of containment bag 300 remains externally of access cannula 100 and the pelvic cavity "U" or, alternatively, may be disposed within access cannula 100 similarly as second open end portion 320 of containment bag 300.

Second and third access cannulas 1100, 2100, respectively, may be inserted through the abdomen into the pelvic cavity "U" to establish triangulation between the access cannulas 100, 1100, 2100. A surgical camera "C" may be inserted through one of the second or third access cannulas 1100, 2100, e.g., third access cannula 2100, to enable visualization of the interior of the pelvic cavity "U."

Figure 8B:
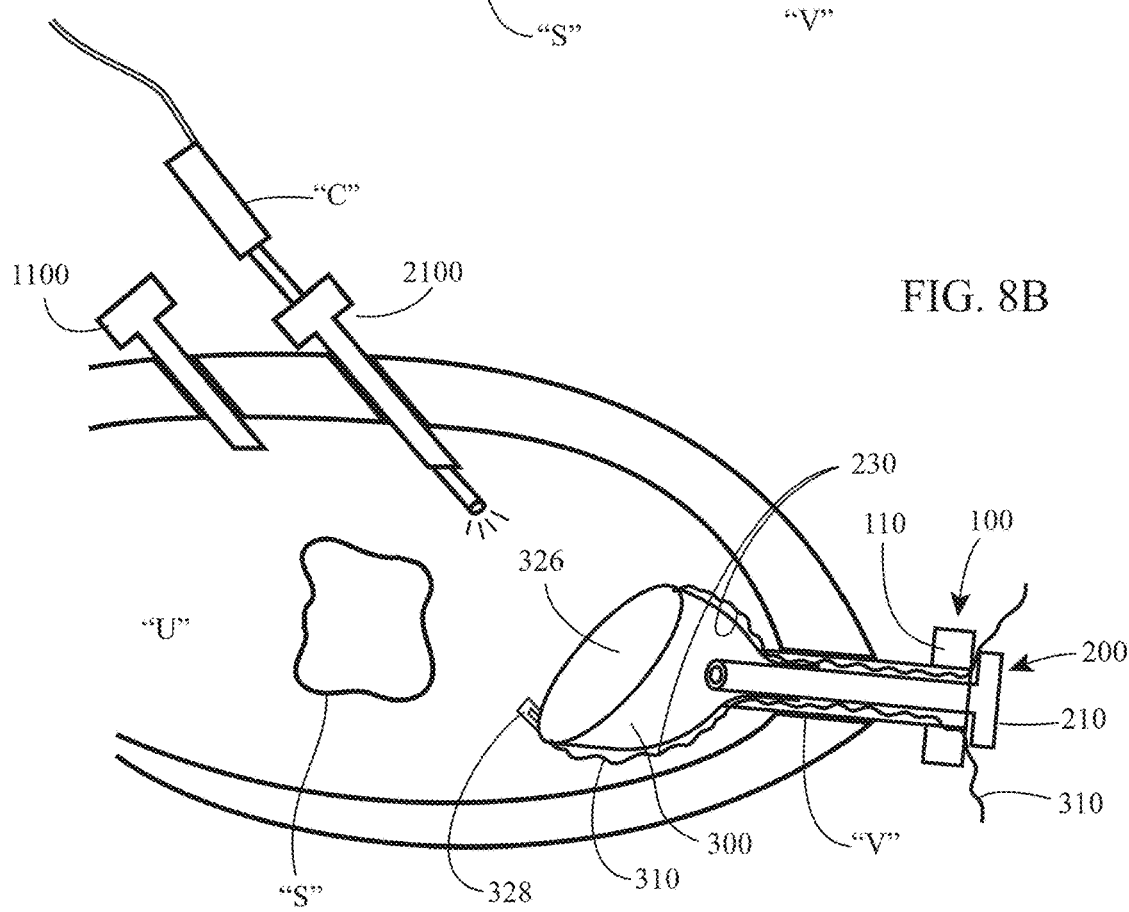

Next, as illustrated in FIG. 8B, system 10 is transitioned from the initial condition to the deployed condition to deploy second open end portion 320 of containment bag 300 into the pelvic cavity "U." As detailed above, deployment of containment bag 300 is accomplished by moving deployment cannula 200 distally through access cannula 100 until proximal hub 210 of deployment cannula 20 is positioned proximally adjacent proximal hub 110 of access cannula 100. As a result of this movement of deployment cannula 200, as also detailed above, engagement fingers 230 are expanded towards the radially-outwardly spaced position and reinforced rim 327 of second open end portion 320 of containment bag 300 is unfurled such that second open end portion 320 of containment bag 300 is expanded and mouth 326 presented to facilitate passage of tissue specimen "S" into second open end portion 320 of containment bag 300.

Figure 8C:
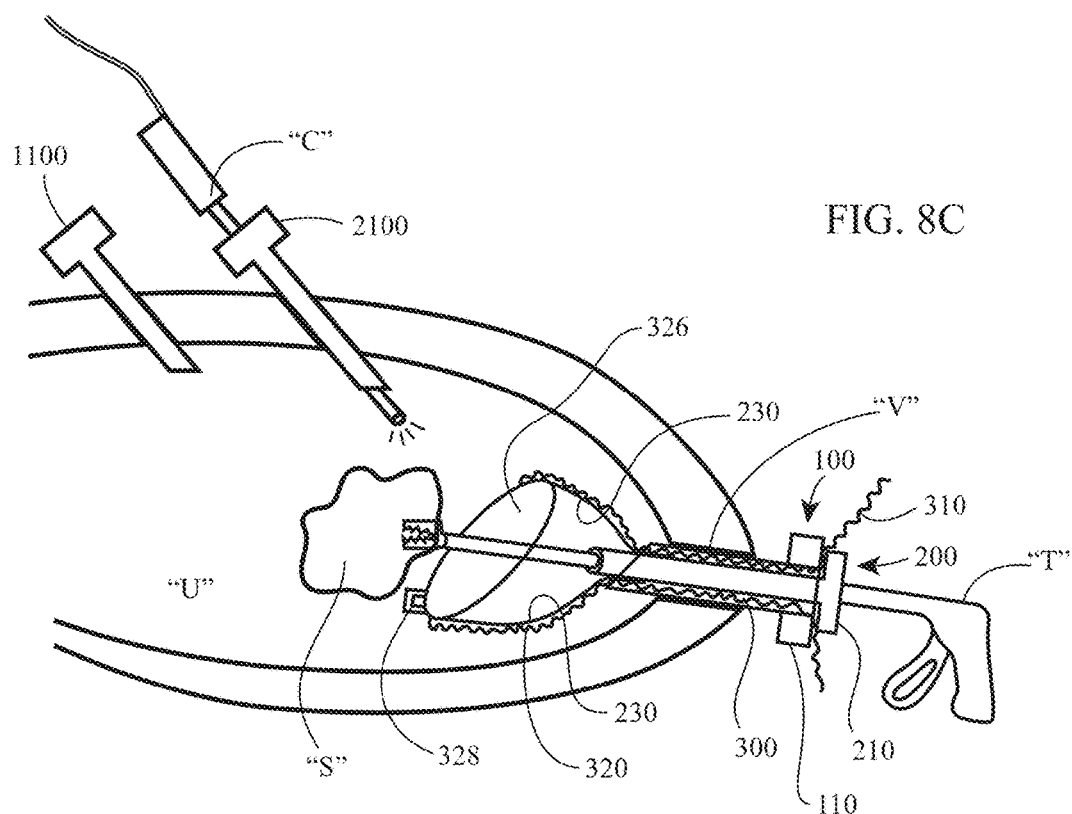
Figure 8D:
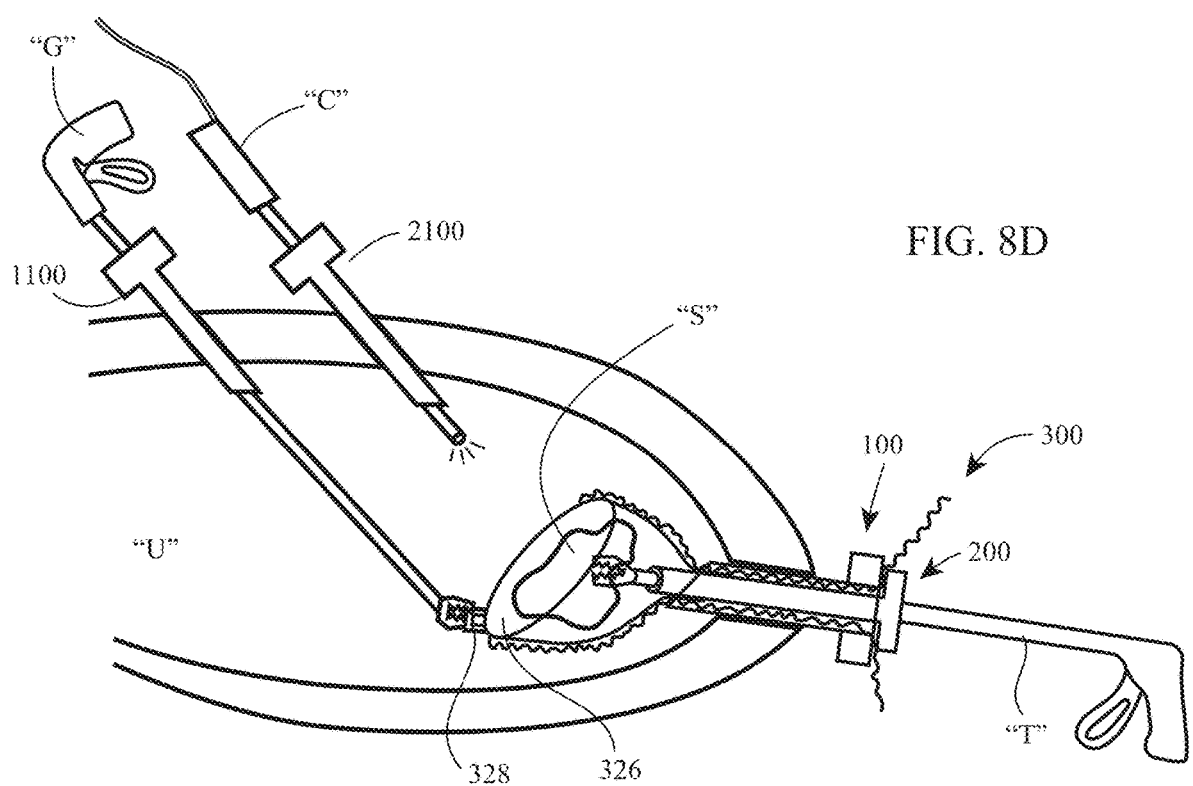

With reference to FIG. 8C, with second open end portion 320 of containment bag 300 deployed within the pelvic cavity "U," a tenaculum "T," or other suitable grasper, may be inserted through lumen 240 of deployment cannula 200 and through containment bag 300 to grasp the tissue specimen "S" and pull the tissue specimen "S" through mouth 326 and into containment bag 300, as illustrated in FIG. 8D. Visualization to facilitate positioning of the tissue specimen "S" within containment bag 300 may be provided via surgical camera "C." The triangulation of access cannulas 100, 1100, 2100 provides an advantageous point of view for surgical camera "C" during the positioning of the tissue specimen "S" within containment bag 300.

Continuing with reference to FIG. 8D, once the tissue specimen "S" is moved into containment bag 300, grasper "G" may be inserted through second access cannula 1100 to grasp tab 328 of containment bag 300. Under visualization from surgical camera "C," with grasper "G" grasping tab 328 of containment bag 300, grasper "G" may be retracted back through second access cannula 1100 bringing second open end portion 320 of containment bag 300 therewith (see also FIG. 8E). Before or after withdrawal of second open end portion 320 of containment bag 300, access cannula 1100 may be removed and re-inserted through second open end portion 320. Alternatively, access cannula 1100 may remain in position with second open end portion 320 of containment bag 300 extending therethrough. Tenaculum "T" may be maintained in position or moved in an opposite direction to ensure the tissue specimen "S" remains within containment bag 300. In either configuration, the triangulation of access cannulas 100, 1100, 2100 provides an advantageous point of view for surgical camera "C" during the retrieval of second open end portion 320 of containment bag 300 from the pelvic cavity "U." Further, containment bag 300 may be insufflated at this point, or at any other suitable juncture, to maximize visualization within containment bag 300.

Figure 8E:
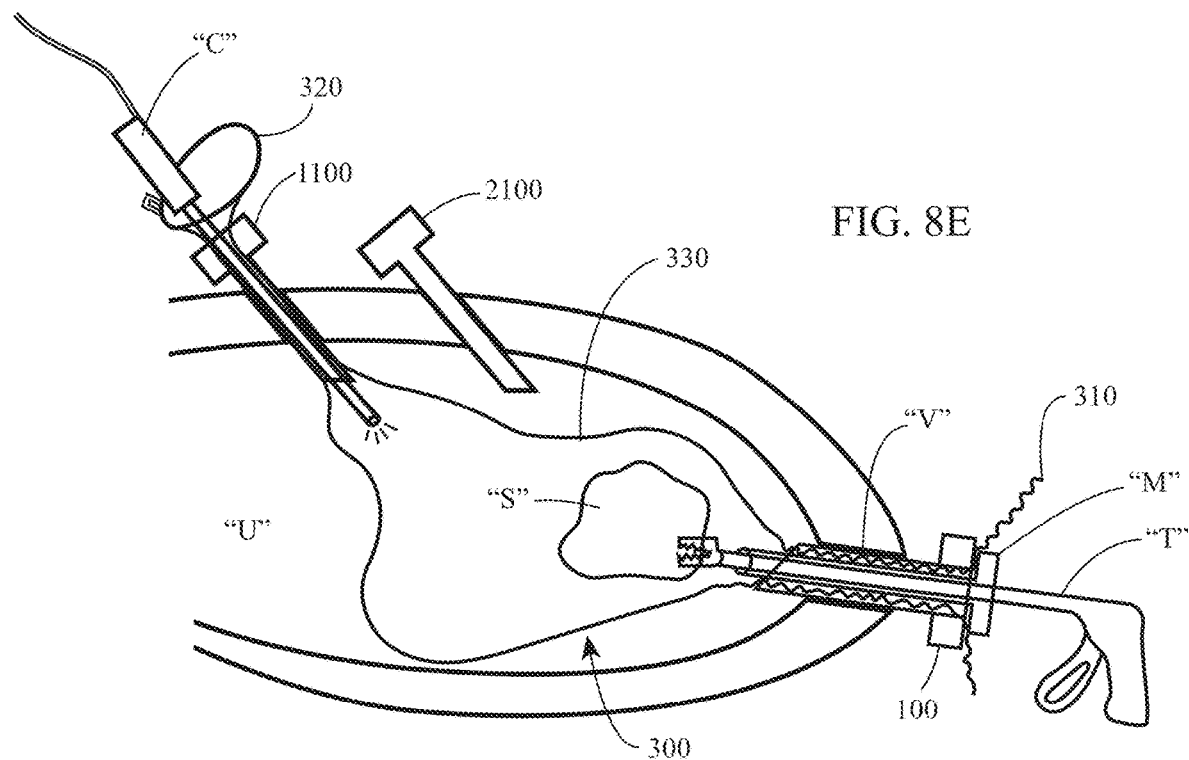
Figure 8F:
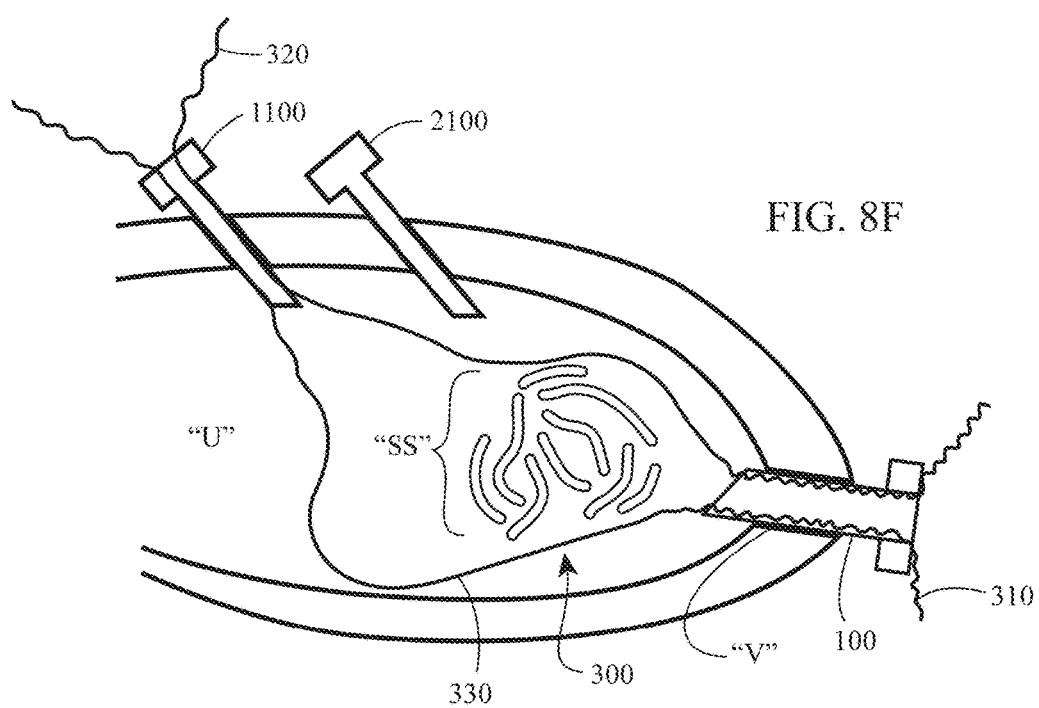

Referring to FIG. 8E, with containment bag 300 containing the tissue specimen "S" within body portion 330 thereof and with first and second open end portions 310, 320, respectively, extending externally of the pelvic cavity "U," tenaculum "T" and deployment cannula 200 may be removed from access cannula 100 in favor of a morcellator "M" that is inserted through first open end portion 310 of containment bag 300 and into body portion 330 thereof adjacent the tissue specimen "S." Alternatively, morecellator "M" may be inserted through second open end portion 320 via access cannula 1100 and surgical camera "C" through first end portion 310 via access cannula 100. In embodiments where morcellator "M" also serves as the deployment cannula 200, no removal is thus required. In either configuration, with additional reference to FIG. 8F, tenaculum "T" may be used in conjunction with morcellator "M" to break down the tissue specimen "S." More specifically, as with respect to the morcellator disclosed in Patent Application Publication No. US 2015/0073429, previously incorporated herein by reference, the tissue specimen "S" may be broken down by cutting the tissue specimen "S" into smaller strips "SS." Other suitable mechanical, electrical, or electromechanical morcellators, for use with or without tenaculum "T," are also contemplated.

Surgical camera "C" may be inserted through second access cannula 1100 and second open end portion 320 of containment bag 300 to provide visualization within containment bag 300 during morcellation of the tissue specimen "S" or, alternatively, may be disposed through third access cannula 2100 to enable visualization through containment bag 300, in embodiments where containment bag 300 is transparent.

Figure 8G:
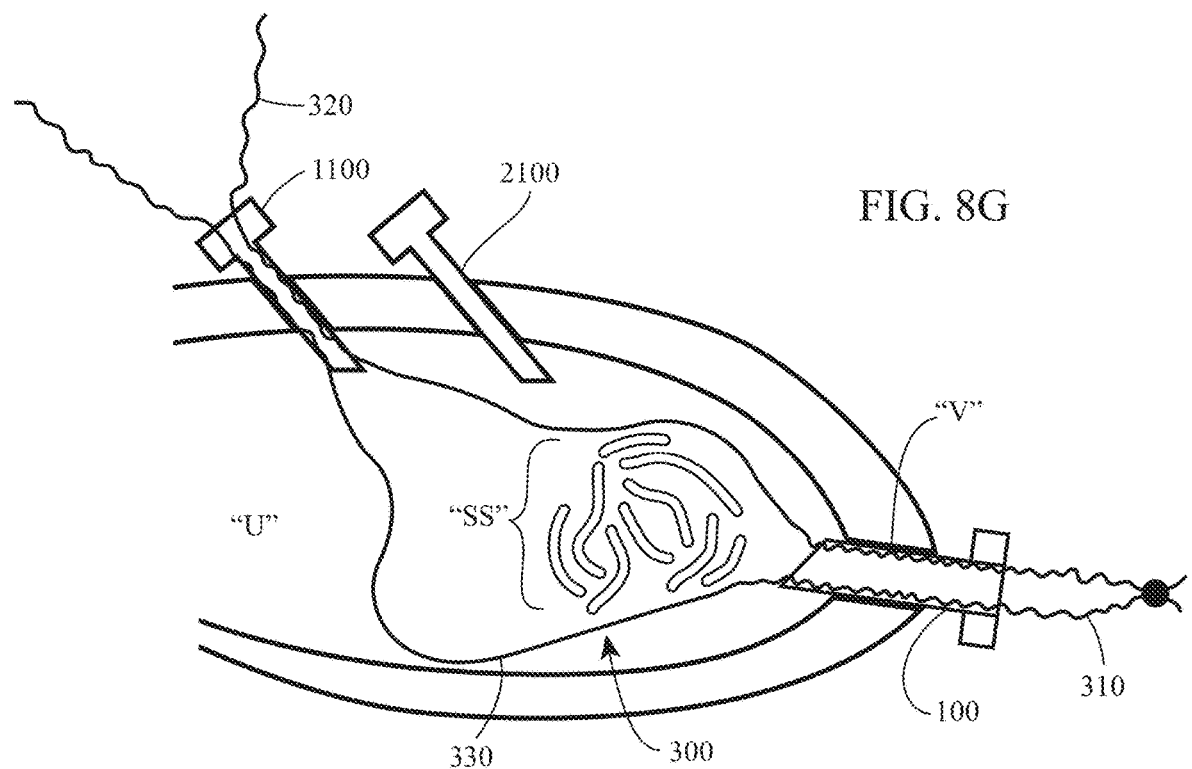
Figure 8H:
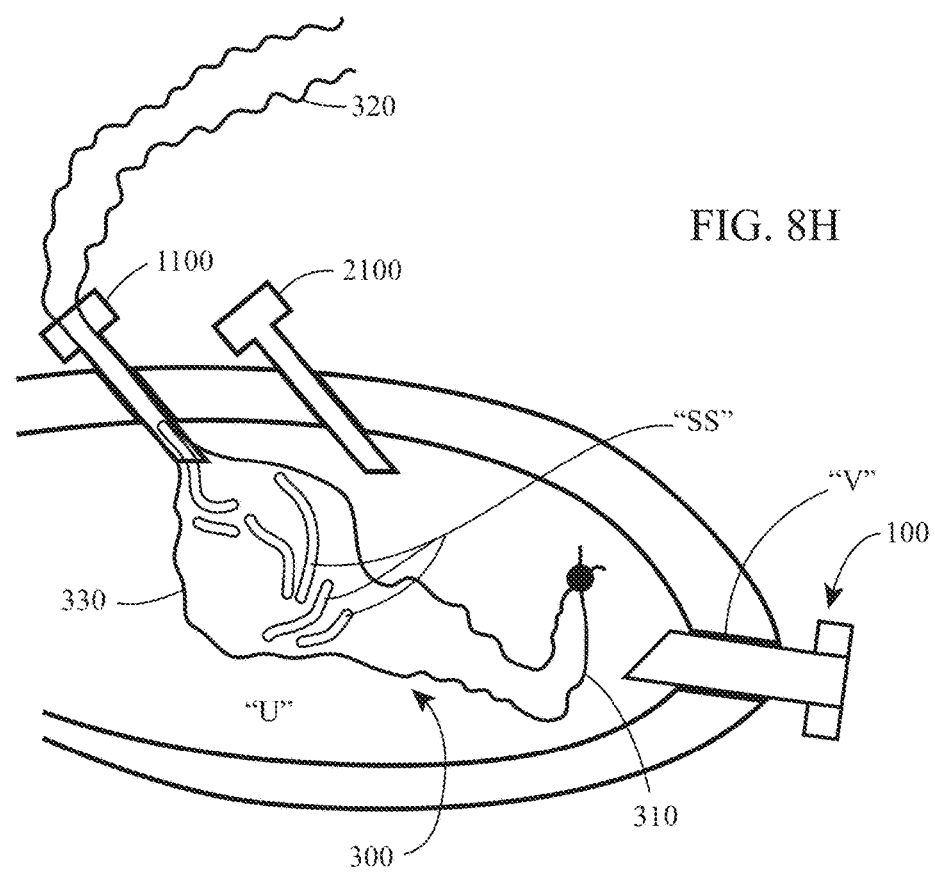

With reference to FIG. 8G, once tissue specimen "S" is sufficiently broken down into smaller strips "SS," morcellator "M" and tenaculum "T" may be removed from access cannula 100 and first open end portion 310 of containment bag 300 sealed off. Alternatively or additionally, second open end portion 320 of containment bag 300 may be sealed off. Referring also to FIG. 8H, containment bag 300 may then withdrawn from the pelvic cavity "U" through one of the abdominal openings such that first open end portion 310 is first pulled into pelvic cavity "U" and follows out through the abdominal opening, e.g., through one of the access cannulas 1100, 2100, or through one of the openings where access cannulas 1100, 2100 were disposed. Alternatively, containment bag 300 may be withdrawn through the vagina "V" such that second open end portion 320 (which is first sealed closed in such embodiments) is first pulled into pelvic cavity "U" and follows out through the vagina "V." In either configuration containment bag 300 may be removed through one of the access cannulas 100, 1100, 2100 or the access cannula(s) 100, 1100, 2100 may be removed prior to withdrawal of containment bag 300.

Turning to FIGS. 9A-9F, another system 3010 is provided in accordance with the present disclosure that facilitates removal of a large tissue specimen from an internal body cavity while maintaining the large tissue specimen in an enclosed environment during break down and removal from the internal body cavity. System 3010 generally includes an access cannula 3100, a deployment cannula 3200 slidably receivable within access cannula 3100, a containment bag 3300 (not shown in FIGS. 9A-9F, see FIGS. 10A-10F) selectively deployable from access cannula 3100, a deployment plunger 3400, and an inner cannula 3500.

Access cannula 3100 may be similar to and/or include any of the features of access cannula 100 (FIG. 1), detailed above. Access cannula 3100 generally includes a proximal hub 3110, an elongated tubular sleeve 3120, and defines a lumen 3140 extending therethrough.

Deployment cannula 3200 includes a proximal hub 3210 and an elongated tubular sleeve 3220 extending distally from proximal hub 3210. Deployment cannula 3200 also defines a lumen 3240 extending therethrough. Proximal hub 3210 includes a base 3212 and an insert 3214 seated within base 3212. Insert 3214 may be removable from base 3212 and retainable therein via friction-fitting (provided by an O-ring 3216 disposed about insert 3214, for example), or may be removably retainable within base 3212 in any other suitable fashion. Thus, insert 3214 may be replaced with a different insert, e.g., insert 3215 (FIG. 9F), having a different configuration, depending upon the instrumentation to be inserted therethrough. Alternatively, insert 3214 may be permanently seated within base 3212. Insert 3214 defines a central aperture 3218, defining the proximal portion of lumen 3240, that is configured to receive inner cannula 3500 and/or other instrumentation therethrough. Insert 3214 further defines a plurality of channels 3219 defined therethrough and positioned radially about central aperture 3218. Channels 3219 are positioned radially outside elongated tubular sleeve 3220. As shown, two diametrically opposed channels 3219 are defined through insert 3214. However, any suitable number and/or positioning of channels 3129 may be provided.

Elongated tubular sleeve 3220 of deployment cannula 3200, as noted above, extends distally from proximal hub 3210. Elongated tubular sleeve 3220 of deployment cannula 3200 defines a reduced diameter as compared to elongated tubular sleeve 3120 of access cannula 3100 so as to define an annular spacing 3222 therebetween when deployment cannula 3200 is received within access cannula 3100. Further, with deployment cannula 3200 received within access cannula 3100, channels 3219 of insert 3214 are aligned and communicate with annular spacing 3222. Elongated tubular sleeve 3220 defines a length sufficiently greater than that of elongated tubular sleeve 3120 of access cannula 3100 such that, with deployment cannula 3200 fully received within access cannula 3100, elongated tubular sleeve 3220 extends distally from elongated tubular sleeve 3120.

Deployment plunger 3400 includes a proximal base 3410 and a plurality of engagement fingers 3430 extending therefrom. Although only two diametrically opposed engagement fingers 3430 are illustrated in the drawings, any suitable number of engagement fingers 3430 may be provided, and may correspond to the number and positioning of channels 3219 of insert 3214 to enable slidable positioning of fingers 3430 through channels 3219 and into annular spacing 3222 defined between elongated tubular sleeve 3220 of deployment cannula 3200 and elongated tubular sleeve 3120 of access cannula 3100. Engagement fingers 3430 are configured as cantilever springs biased radially-outwardly in the at-rest positions thereof. However, when received within channels 3219 and/or annular spacing 3222, engagement fingers 3430 are retained in a substantially linear configuration against the bias thereof. Engagement fingers may further be configured similar to engagement fingers 230, detailed above (FIG. 3.)

Inner cannula 3500 includes a proximal hub 3510 and an elongated tubular sleeve 3520 extending distally from proximal hub 3510. Inner cannula 3500 also defines a lumen 3540 extending therethrough. Proximal hub 3510 is configured for insertion at least partially into central aperture 3218 of insert 3214 of deployment cannula 3200 and may be releasably retainable therein via friction-fitting (provided by an O-ring 3512 disposed about proximal hub 3510, for example). Proximal hub 3510 further defines a central opening 3518, defining the proximal end of lumen 3540, that is configured to receive instrumentation therethrough.

Elongated tubular sleeve 3520 of inner cannula 3500, as noted above, extends distally from proximal hub 3510. Elongated tubular sleeve 3520 of inner cannula 3500 defines a reduced diameter as compared to elongated tubular sleeve 3220 of deployment cannula 3200 so as to define an annular spacing 3522 therebetween when inner cannula 3500 is received within deployment cannula 3200. Further, elongated tubular sleeve 3520 defines a length sufficiently greater than that of elongated tubular sleeve 3220 of deployment cannula 3200 such that, with proximal hub 3510 fully seated within central aperture 3218 of insert 3214 of deployment cannula 3200, elongated tubular sleeve 3520 extends further distally than elongated tubular sleeve 3220. As such, with inner cannula 3500 fully received within deployment cannula 3200 and with deployment cannula 3200 fully received within access cannula 3100, elongated tubular sleeve 3520 also extends distally from elongated tubular sleeve 3120.

With additional reference to FIGS. 10A-10F, containment bag 3300 may be configured similar to containment bag 300 (FIGS. 3-7C), detailed above, and may include any or all of the features thereof. Containment bag 3330, similar to containment bag 300 (FIGS. 3-7C), is configured for positioning, in an initial condition of system 3010, within access cannula 3100, and is deployable therefrom to a deployed condition of system 3010, wherein containment bag 3300 is deployed into the internal body cavity under urging from deployment cannula 3200, deployment plunger 3400, and inner cannula 3500, and is unfurled, thus presenting containment bag 3300 to enable positioning of a tissue specimen therein. Containment bag 3330 may be fully deployed into the internal body cavity, or a portion of containment bag 3300 may extend proximally from access cannula 3100 and remain externally thereof, similarly as detailed above with respect to containment bag 300 (FIGS. 8A-8H). Alternatively, one end portion of containment bag 3300 may be attached (removably or permanently) to one of the components of system 3010, e.g., access cannula 3100, deployment cannula 3200, or inner cannula 3500. Likewise, in other embodiments, rather than being externalized, one end portion of the containment bag may be attached to one of the components of the deployment system thereof. Such a configuration allows for access of different devices (e.g., tenaculum, grasper, morcellator, etc.) into the specimen bag while maintaining pneumoperitoneum, and also helps control the excess bag material and improve usability. Further, as detailed below, containment bag 3300 may be deployed into the internal body cavity in two or more stages, although a single, continuous deployment is also contemplated.

In the initial condition of system 3010, a distal portion of containment bag 3300 (including the furled, reinforced rim thereof), is maintained within lumen 3140 of access cannula 3100 distally of deployment cannula 3200; an intermediate portion of containment bag 3300 is disposed within annular spacing 3222 defined between elongated tubular sleeve 3220 of deployment cannula 3200 and elongated tubular sleeve 3120 of access cannula 3100; and a proximal portion of containment bag 3300 is disposed within annular spacing 3522 defined between elongated tubular sleeve 3520 of inner cannula 3500 and elongated tubular sleeve 3220 of deployment cannula 3200, although part of the proximal portion may also extend proximally from deployment cannula 3200 and remain externally, similarly as detailed above with respect to system 10 (FIGS. 8A-8H). Other configurations for containment bag 3300, in the initial condition of system 3010, are also contemplated.

Deployment of containment bag 3300 from the above-noted initial condition of system 3010 to the deployed condition thereof, as detailed below, is effected in a plurality of stages: initially by distal advancement of deployment cannula 3200 relative to access cannula 3100 to deploy the distal portion of containment bag 3300; further via distal advancement of deployment plunger 3400 relative to deployment cannula 3200 and access cannula 3100 to deploy the intermediate portion of containment bag 3300; and, finally, by withdrawal and re-insertion of access cannula 3500 to and from deployment cannula 3200, to deploy some or all of the proximal portion of containment bag 3300.

Referring to FIGS. 10A-10F, in conjunction with FIGS. 9A-9F, the use of system 3010 in the removal of a large tissue specimen "S" from the pelvic cavity "U," maintaining the large tissue specimen "S" in an enclosed environment during break down and removal, is described. System 3010 may be similarly used in the removal of other tissue specimen from other internal body cavities. Further, use of system 3010 and additional instrumentation used therewith, e.g., abdominal ports, surgical cameras, graspers, etc., are similar to that detailed above with respect to system 10 (FIGS. 8A-8H) and, thus, only differences will be detailed below while similarities are summarily described or omitted entirely for purposes of brevity.

Referring initially to FIGS. 9A and 10A, with system 3010 disposed in the initial condition, access cannula 3100 is advanced through the vagina "V" into the pelvic cavity "U" or, if the cervix is still intact, through the vagina "V" and an incision in the posterior vaginal fornix into the pelvic cavity "U." Next, as illustrated in FIGS. 9B and 10B, system 3010 is transitioned from the initial condition to a partially-deployed condition to deploy the distal portion of containment bag 3300 into the pelvic cavity "U." This partial deployment is accomplished by moving deployment cannula 3200, together with deployment plunger 3400, distally relative to access cannula 3100 until proximal hub 3210 of deployment cannula 3200 is positioned proximally adjacent proximal hub 3110 of access cannula 3100. Although deployment plunger 3400 is moved distally, it remains fixed relative to deployment cannula 3200, whereby proximal base 3410 of deployment plunger 3400 is proximally-spaced from proximal hub 3210 of deployment cannula 3200. As a result of the above-detailed movement of deployment cannula 3200 and deployment plunger 3400, the distal end of deployment cannula 3200 urges the distal portion of containment bag 3300 distally from lumen 3140 of access cannula 3100 and into the pelvic cavity "U." In addition, engagement fingers 3430 of deployment plunger 3400 are partially extended into the pelvic cavity "U" to facilitate deployment of containment bag 3300. However, the majority of containment bag 3330 remains disposed within access cannula 3100.

With reference to FIGS. 9C and 10C, in order to further deploy containment bag 3300 about tissue specimen "S," a tenaculum "T" is inserted through inner cannula 3500 and into the pelvic cavity "U" to grasp the tissue specimen "S" and either maintain the tissue specimen "S" in position or pull the tissue specimen "S" towards access cannula 3100. With the tenaculum "T" grasping the tissue specimen "S," deployment plunger 3400 is advanced distally relative to access cannula 3100 and deployment cannula 3200 such that engagement arms 3420 are advanced distally through channels 3219, annular spacing 3222, and further into the pelvic cavity "U" to urge containment bag 3300 distally from access cannula 3100 further into the pelvic cavity "U" and about the tissue specimen "S." Engagement arms 3420 may be configured to engage containment bag 3300 similarly as detailed above with respect to system 10 (FIGS. 8A-8H) to facilitate deployment thereof, or may be configured to deploy containment bag 3300 in any other suitable fashion.

Referring also to FIGS. 9D, 9E, 10D, and 10E, in order to complete deployment of containment bag 3300, deployment plunger 3400 is retracted proximally back to its initial position, or removed entirely. In addition, inner cannula 3500 is momentarily withdrawn proximally from deployment cannula 3200, allowing the portion of containment bag 3300 disposed within annular spacing 3322 to collapse into lumen 3240 of deployment cannula 3200 and occupy more space thereof. Inner cannula 3500 may then be re-inserted into deployment cannula 3200 to urge the repositioned portion of containment bag 3300 distally therefrom and into the pelvic cavity "U."

Prior to or after withdrawal and re-insertion of inner cannula 3500, the distal portion of containment bag 3300 may be withdrawn through an abdominal port, similarly as detailed above with respect to system 10 (FIGS. 8A-8H).

Figure 9E:
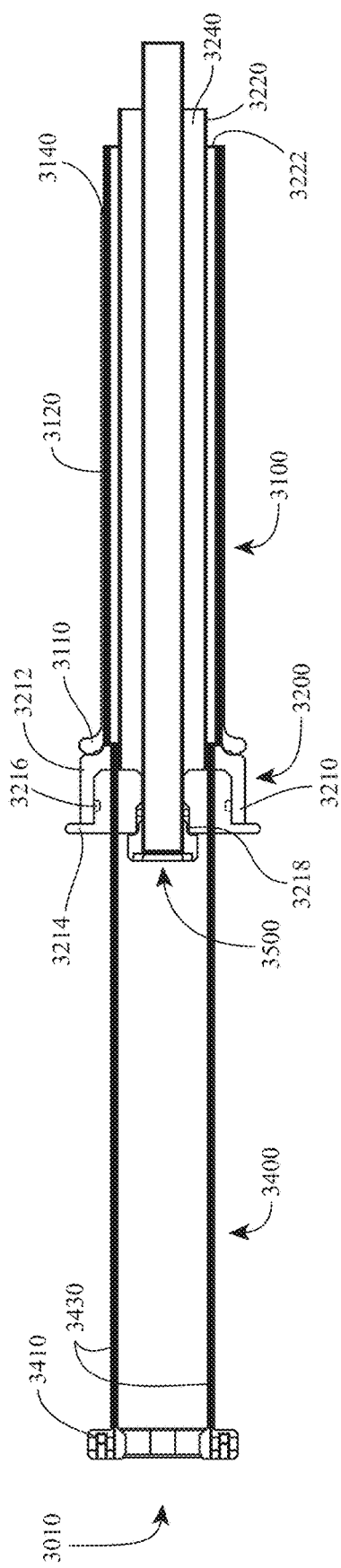
Figure 9F:
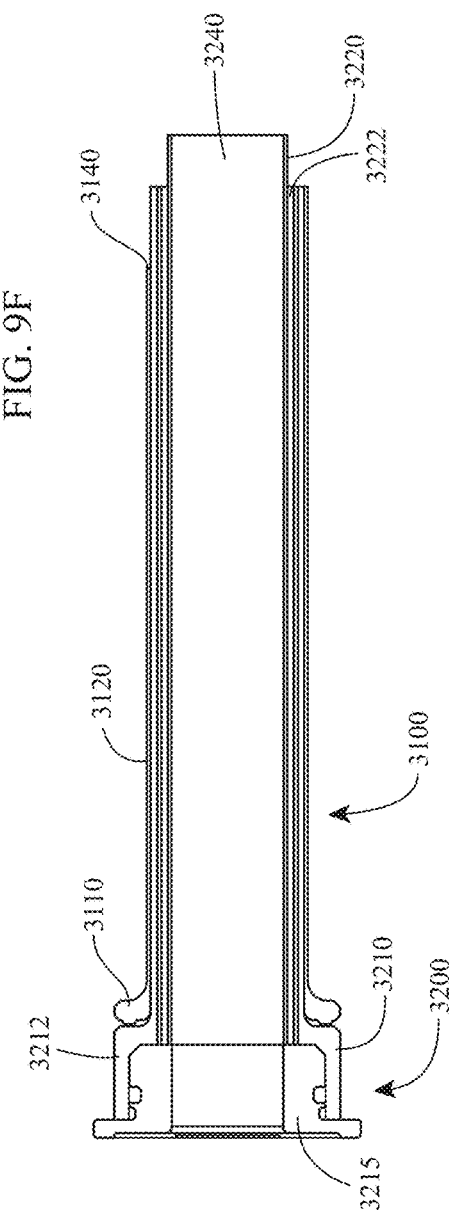

Next, as shown in FIGS. 9F and 10F, inner cannula 3500 may once again be removed, along with deployment plunger 3400 (if not removed already). If necessary, insert 3214 may be replaced with a different insert 3215 having a different, e.g., larger, internal diameter, and a morcellator "M" inserted through insert 3215 and through deployment cannula 3200 into the pelvic cavity "U." Of course, if replacement is not required, e.g., if a larger diameter is not needed, insert 3214 may be utilized. Insufflation of containment bag 3300 may also be accomplished at this point, if required. Once morcellator "M" is inserted into position, tenaculum "T" may be inserted through morcellator "M" to grasp and/or manipulate the tissue specimen "S" during morcellation. Completion of morcellation and removal of the containment bag 3300 with the tissue specimen "S" therein may be accomplished similarly as detailed above with regard to system 10 (FIGS. 8A-8H). Further, similarly as detailed above with regard to system 10 (FIGS. 8A-8H), some or all of the above may be performed under observation using a surgical camera inserted from an abdominal port.

Turning to FIGS. 11A-11F, another containment bag provided in accordance with the present disclosure is shown generally identified by reference numeral 4300. Containment bag 4300 may be similar to and include any or all of the features of containment bag 300 (FIGS. 4-6) except that, rather than a grasping tab 328 (FIGS. 4-6) to facilitate manipulation of the second open end portion within an internal body cavity, insertion of a tissue specimen through the second open end portion, and/or withdrawal of the second open end portion from the internal body cavity, containment bag 4300 includes a suture arrangement 4330. Containment bag 4300 may be utilized in conjunction with any or all of the devices, systems, and methods detailed above.

Suture arrangement 4330 includes a plurality of sutures, e.g., first, second, and third sutures 4332, 4334, 4336, respectively. However, although three (3) sutures 4332, 4334, 4336 are illustrated and described herein, any suitable number of sutures may be provided. Sutures 4332, 4334, 4336 are attached at first ends thereof to second open end portion 4320 of containment bag 4300 about the annular periphery thereof. More specifically, sutures 4332, 4334, 4336 are spaced-apart about at least a portion of the annular periphery of second open end portion 4320 of containment bag 4300. In embodiments, the first ends of sutures 4332, 4334, 4336 are equally-spaced about at least a portion of the annular periphery of second open end portion 4320 of containment bag 4300. However, sutures 4332, 4334, 4336 need not be equally-spaced, nor do sutures 4332, 4334, 4336 need to extend about the entire annular periphery of second open end portion 4320 of containment bag 4300. Rather, the first ends of sutures 4332, 4334, 4336 may be disposed in any suitable configuration to facilitate manipulation of second open end portion 4320 of containment bag 4300, insertion of a tissue specimen "S" through the second open end portion 4320 and into containment bag 4300, and/or withdrawal of second open end portion 4320 from an internal body cavity, e.g., the pelvic cavity "U."

Figure 11A:
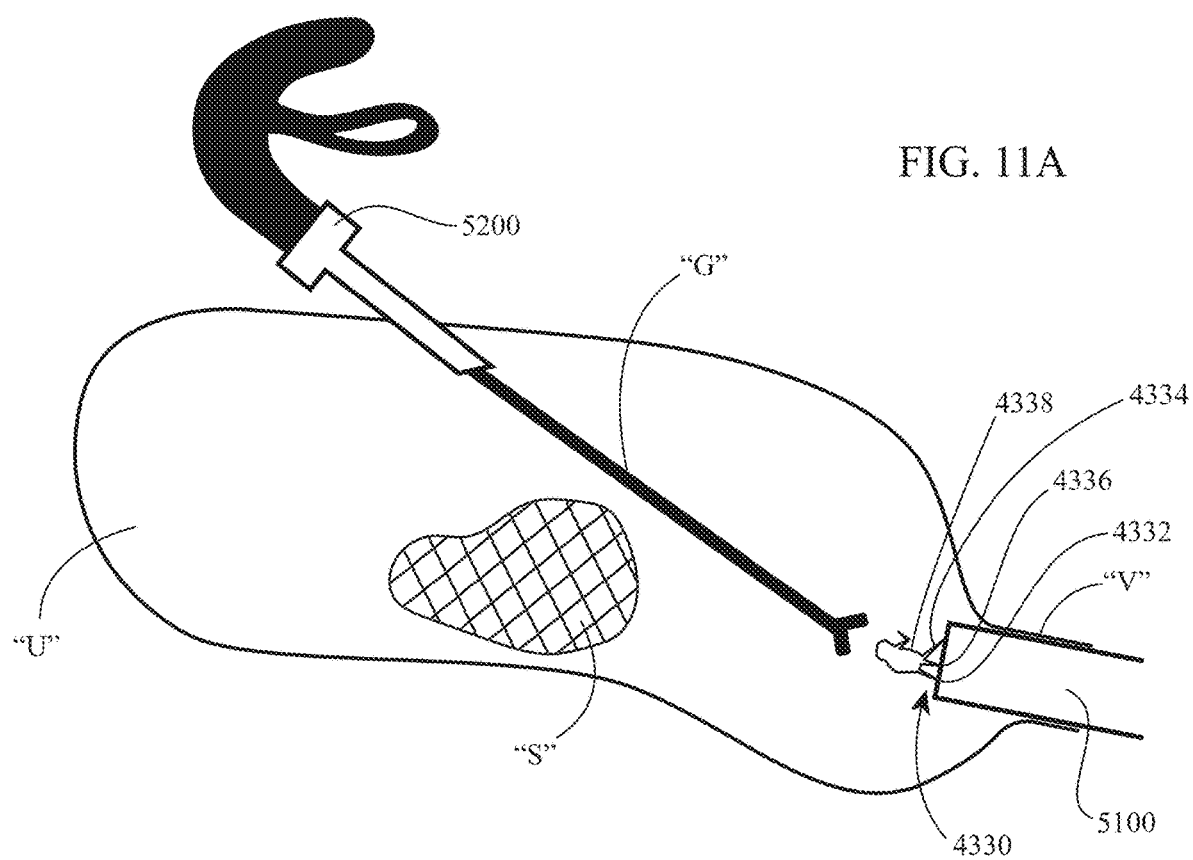
FIGS. 11A-11F illustrate another containment bag provided in accordance with the present disclosure and the use thereof in conjunction with a tissue specimen removal system to enclose a tissue specimen therein within an internal body cavity.

The second ends of sutures 4332, 4334, 4336 may be joined to one another via knotting or in any other suitable manner or via any other suitable mechanism such as, for example, using a cuff 4338 (FIG. 11A). Alternatively, the second ends of sutures 4332, 4334, 4336 may remain unattached. In embodiments where the second ends of sutures 4332, 4334, 4336 are attached, and as detailed below, the second ends of sutures 4332, 4334, 4336 may collectively be withdrawn from the pelvic cavity "U" through a single access cannula, e.g., additional access cannula 5200. In embodiments where the second ends of sutures 4332, 4334, 4336 remain unattached, on the other hand, the second ends of two or more of the sutures 4332, 4334, 4336 may be withdrawn from the pelvic cavity "U" through different access cannulas, although they may also be withdrawn through the same access cannula.

In embodiments, additional sutures (not shown) may be attached to one or more of sutures 4332, 4334, 4336 towards either end thereof, at either end thereof, or at an intermediate portion thereof. The additional sutures (not shown), for example, may extend between and interconnect intermediate portions of sutures 4332, 4334, 4336, or may extend from one or more of sutures 4332, 4334, 4336 with the second ends thereof joined with the second ends of sutures 4332, 4334, 4336. Other suitable configurations are also contemplated.

Suture arrangement 4330 provides triangulation about second open end portion 4320 of containment bag 4300. This triangulation, more specifically, allows sutures 4332, 4334, 4336 to be grasped and manipulated to maneuver second open end portion 4320 of containment bag 4300 within the pelvic cavity "U" while maintaining second open end portion 4320 of containment bag 4300 in proper orientation to accept the tissue specimen "S" therethrough. This triangulation also facilitates advancement of second open end portion 4320 of containment bag 4300 about the tissue specimen "S" via manipulating sutures 4332, 4334, 4336, and, ultimately, withdrawal of sutures 4332, 4334, 4336 and second open end portion 4320 of containment bag 4300 from the pelvic cavity "U."

In use, with reference to FIG. 11A, containment bag 4300 is initially disposed within a cannula 5100 (which may be the cannula of any of the systems disclosed hereinabove or any other suitable cannula or cannula system) in an initial condition and cannula 5100 is advanced through the vagina "V" into the pelvic cavity "U" or, if the cervix is still intact, through the vagina "V" and an incision in the posterior vaginal fornix into the pelvic cavity "U." One or more access cannulas 5200 may be inserted through the abdomen into the pelvic cavity "U," prior to or after insertion of cannula 5100.

Figure 11B:
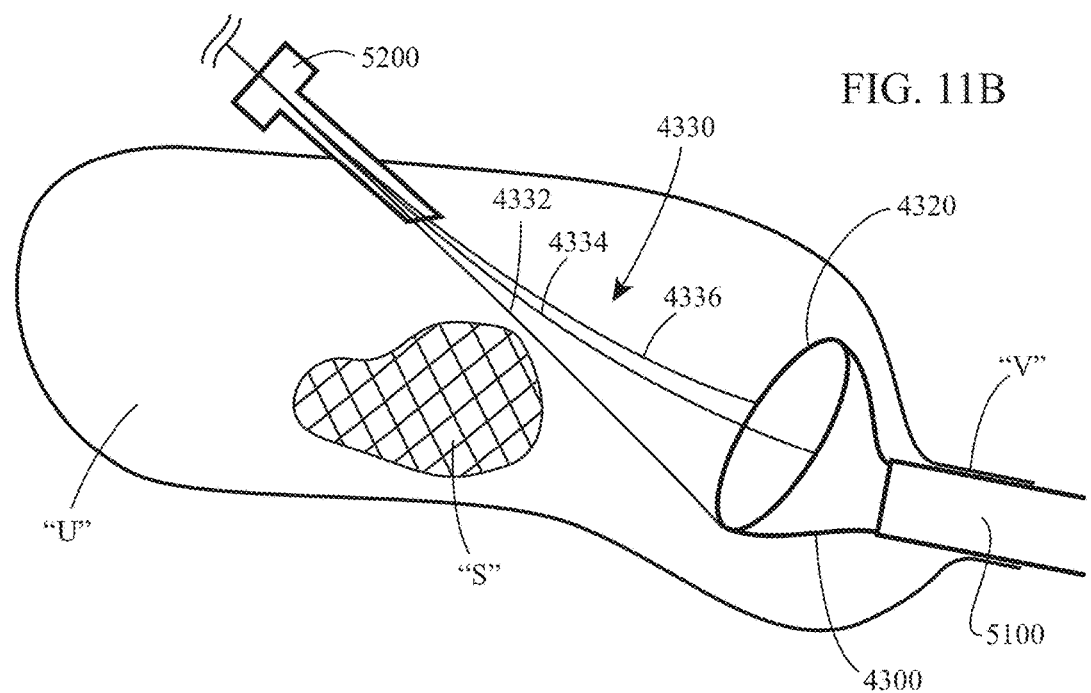

With additional reference to FIG. 11B, one or more graspers "G" may be inserted through the one or more additional access cannulas 5200 and manipulated to grasp the second ends of sutures 4332, 4334, 4336 (collectively or independently) of suture arrangement 4330. More specifically, in embodiments where the second ends of sutures 4332, 4334, 4336 are attached to one another, e.g., via cuff 4338, one grasper "G" may be utilized to grasp cuff 4338 and pull cuff 4338 through the pelvic cavity "U" towards additional access cannula 5200. In this manner, second open end portion 4320 of containment bag 4300 is deployed from cannula 5100 and into the pelvic cavity "U."

Figure 11C:
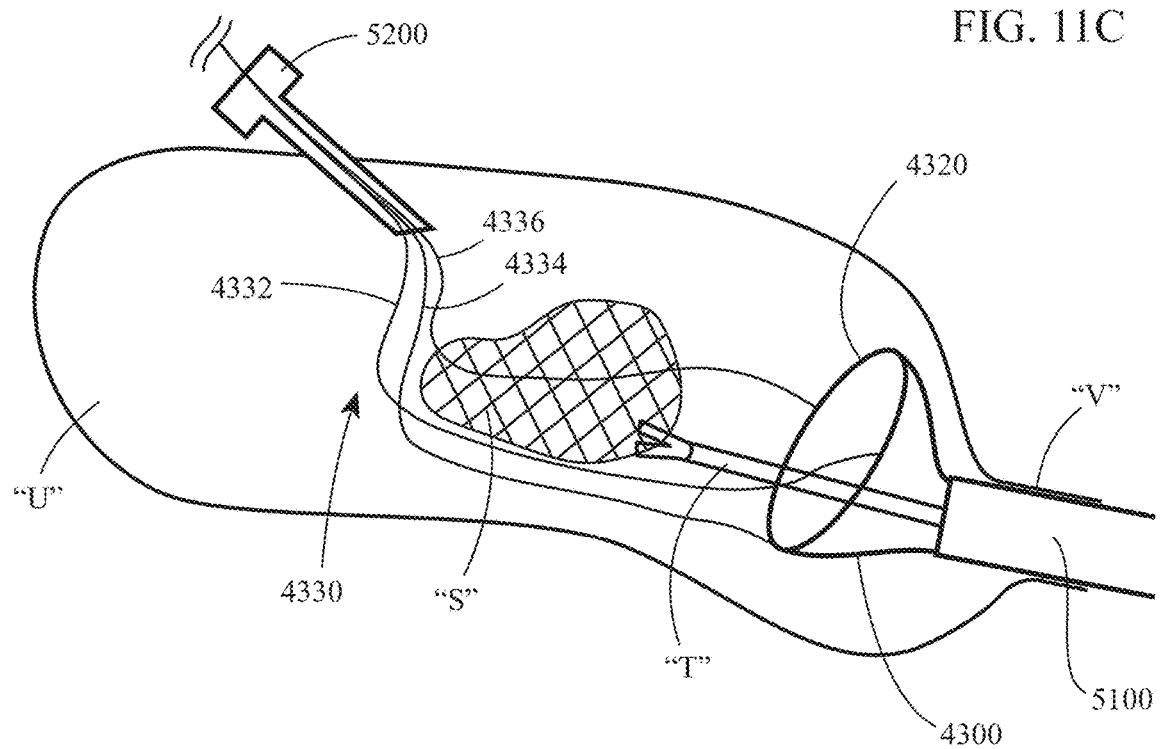
Figure 11D:
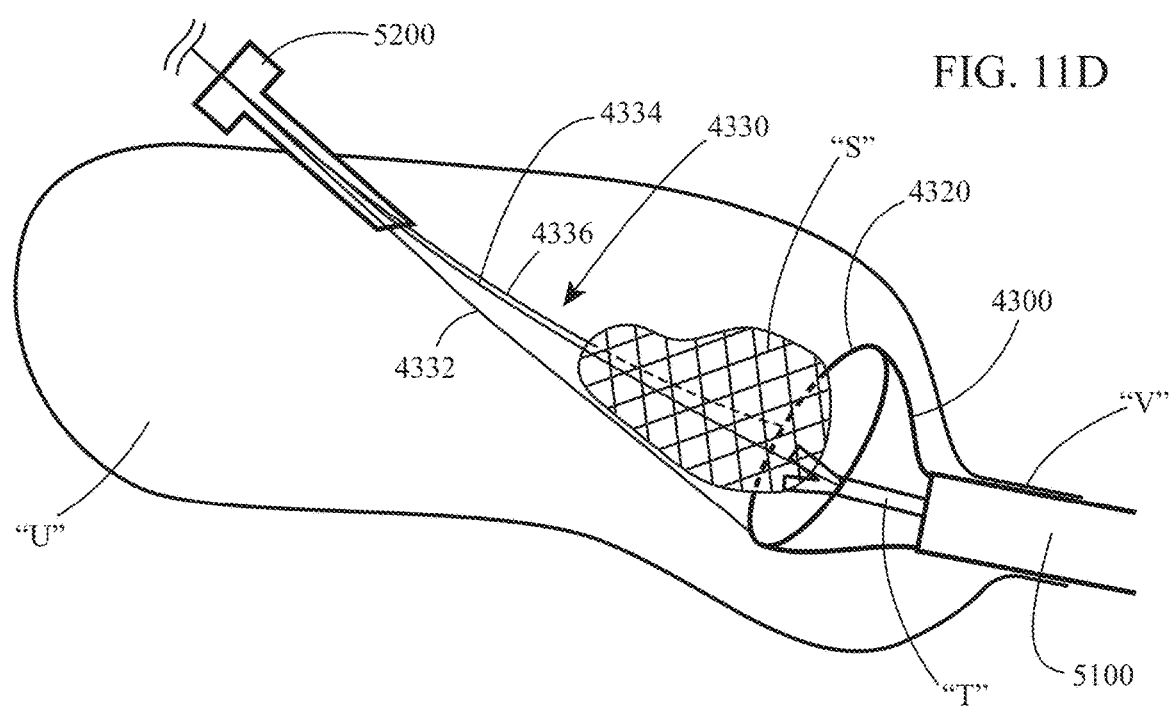
Figure 11E:
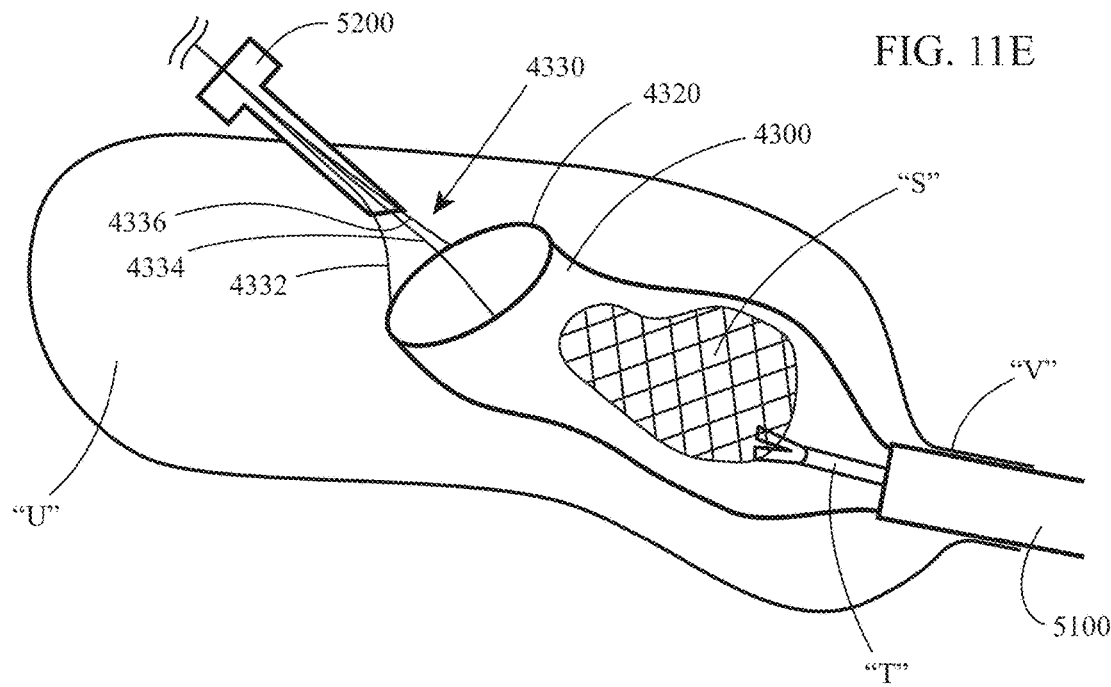

Referring to FIGS. 11C-11E, with second open end portion 4320 of containment bag 4300 deployed within the pelvic cavity "U," a tenaculum "T," or other suitable grasper, may be inserted through cannula 5100 and through containment bag 4300 to grasp the tissue specimen "S." With the tenaculum "T" grasping the tissue specimen "S" to maintain the tissue specimen "S" stationary or drawing the tissue specimen "S" proximally towards cannula 5100, the second ends of sutures 4332, 4334, 4336 are pulled in a generally opposing direction such that second open end portion 4320 of containment bag 4300 is likewise pulled in the generally opposing direction, e.g., towards additional access cannula 5200. As detailed above, the triangulation provided by suture arrangement 4330 helps ensure that second open end portion 4320 of containment bag 4300 is maintained in an open condition and oriented towards the tissue specimen "S" as it is pulled towards about the tissue specimen "S" such that the tissue specimen "S" is received within second open end portion 4320 of containment bag 4300. Ultimately, the second ends of sutures 4332, 4334, 4336 are pulled out of the pelvic cavity "U" through additional access cannula 5200.

Figure 11F:
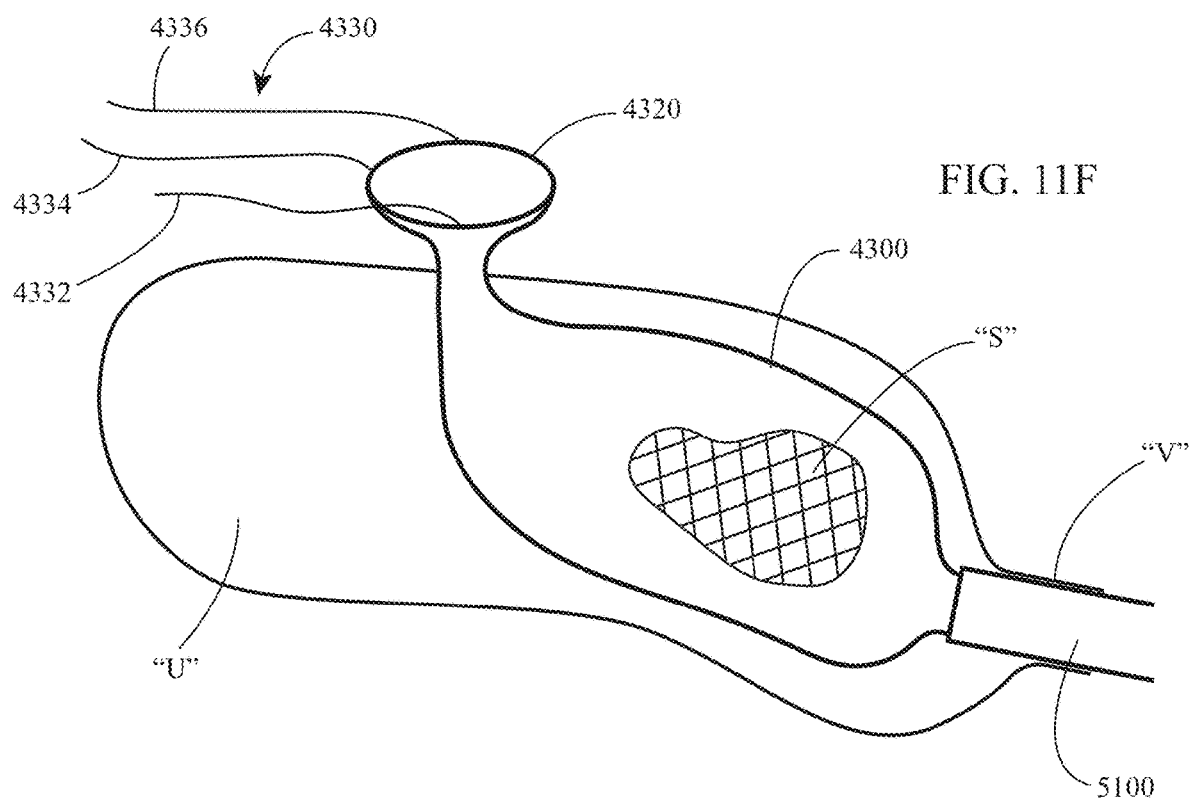

With additional reference to FIG. 11F, the second ends of sutures 4332, 4334, 4336 are withdrawn through additional access cannula 5200 sufficiently such that sutures 4332, 4334, 4336 and second open end portion 4320 of containment bag 4300 are likewise pulled out of the pelvic cavity "U" through additional access cannula 5200, leaving the tissue specimen "S" disposed within containment bag 4300 within the pelvic cavity "U" with the first open end portion of containment bag 4300 and second open end portion 4320 thereof extending through different cannulas 5100, 5200 externally of the pelvic cavity "U." The above-detailed use of containment bag 4300 may otherwise be similar to and include any of the features of the above-described devices, systems, and methods. For example, the tissue specimen "S" may be broken down by cutting the tissue specimen "S" into smaller strips "SS" (FIGS. 8F-8H) to facilitate removal from the pelvic cavity "U," the first open end portion of containment bag 4300 may be sealed off, and containment bag 4300 may be withdrawn from the pelvic cavity "U" through additional access cannula 5200.

Figure 12:
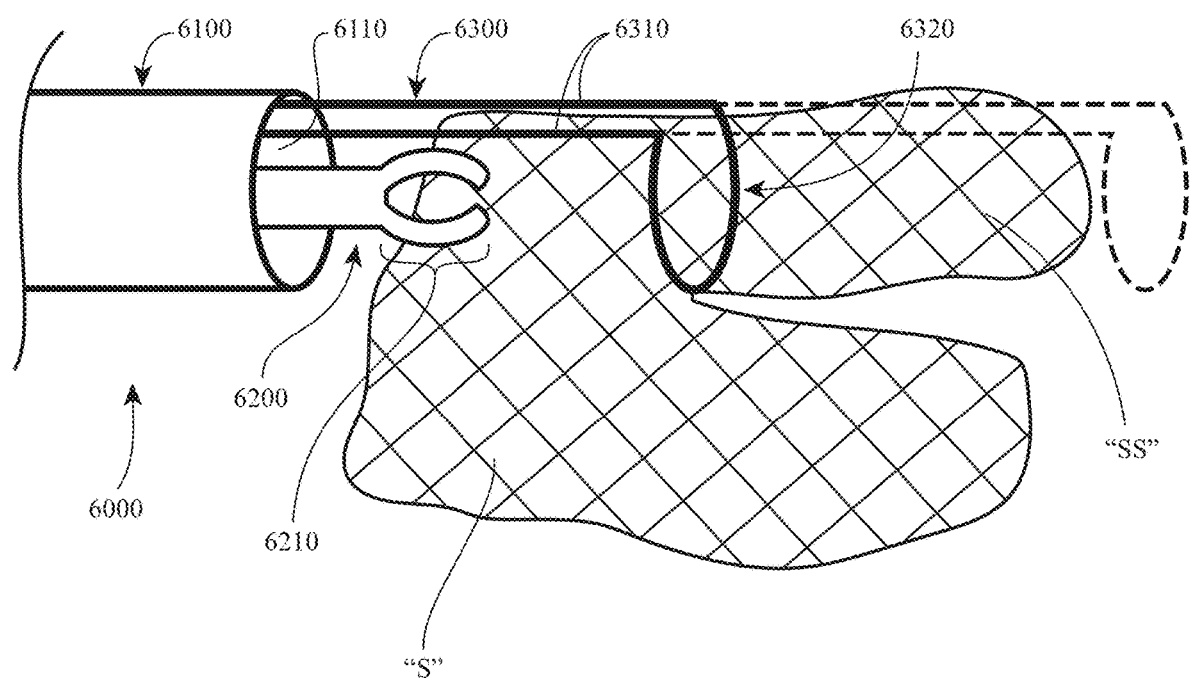
FIG. 12 illustrates a tissue-strip cutting device provided in accordance with the present disclosure shown in use breaking down a tissue specimen into smaller tissue strips.

Turning now to FIG. 12, as mentioned above, the tissue specimen "S" may be broken down by cutting the tissue specimen "S" into smaller strips "SS" to facilitate removal from the pelvic cavity "U." A tissue-strip cutting device provided in accordance with the present disclosure and suitable for the purpose is detailed below and generally identified by reference numeral 6000. Tissue-strip cutting device 6000 is not limited for use with the devices, systems, and methods detailed herein but, rather, may be used with various other devices, systems, and methods to cut a tissue specimen "S" into smaller strips "SS." Similarly, the above-detailed devices, systems, and methods need not employ tissue-strip cutting device 600 but may utilize any other suitable device(s) for cutting the tissue specimen "S" into smaller strips "SS."

Tissue-strip cutting device 6000 includes an elongated tubular member 6100, a grasper 6200, and a cutting element 6300. Elongated tubular member 6100, grasper 6200, and cutting element 6300 may be coupled to one another as part of an integral device or may be separate from one another. Elongated tubular member 6100 may be insertable through an access cannula, e.g., through access cannula 100 and into containment bag 300 (FIGS. 8E-8F), or may be an access cannula itself. In either configuration, elongated tubular member 6100 defines a lumen 6110 extending longitudinally therethrough.

Grasper 6200 is configured to extend through lumen 6110 of elongated tubular member 6100 and distally therefrom such that working end 6210 of grasper 6200 may extend into an internal surgical site, e.g., into containment bag 300 disposed within the pelvic cavity "U" (see FIGS. 8E-8F), for positioning adjacent the tissue specimen "S" to be cut into smaller strips "SS." Grasper 6200 is configured to grasp a portion of the tissue specimen "S" to maintain the tissue specimen "S" in substantially fixed position relative to grasper 6200 and elongated tubular member 6100. Working end 6210 may include a pair of pivotable jaw members 6220, or any other suitable component(s), that enable grasping of the tissue specimen "S" therewith.

Cutting element 6300 includes a pair of elongated, spaced-apart rods 6310 interconnected at their respective distal ends via a U-shaped loop 6320 that depends from rods 6310. Rods 6310 are formed at least partially from an electrically-conductive material and may be covered with an insulative coating or sheath (not shown). U-shaped loop 6320 is likewise formed from an electrically-conductive material and may be integral with or engaged and electrically coupled to rods 6310. Either or both of rods 6310 is adapted to connect to a source of electrosurgical energy, e.g., RF energy, to enable the selective energization of U-shaped loop 6320. U-shaped loop 6320 may function as a monopolar electrode for use with a remote return pad (not shown), or may function as one electrode in a bipolar configuration, with another component, e.g., a portion of grasper 6200, a portion of elongated tubular member 6100, or other suitable component, severing as the other electrode.

Cutting element 6300 is configured to extend through lumen 6110 of elongated tubular member 6100 and distally therefrom. More specifically, cutting element 6300 is selectively translatable through and relative to elongated tubular member 6100 between a distal position (illustrated in phantom in FIG. 12), wherein U-shaped loop 6320 is further-spaced distally from elongated tubular member 6100, and a proximal position (illustrated in FIG. 12), wherein U-shaped loop 6320 is closer to elongated tubular member 6100. As detailed below, movement of cutting element 6300 from the distal position to the proximal position while energy is supplied to U-shaped loop 6320 serves to cut an elongated strip "SS" of tissue from tissue specimen "S."

Continuing with reference to FIG. 12, in use, elongated tubular member 6100 is inserted through an access cannula or directly into the internal surgical site adjacent the tissue specimen "S" to be broken down and removed. As noted above, in embodiments, elongated tubular member 6100 may be inserted into a containment bag, e.g., containment bag 300 (FIG. 8E), disposed within the internal surgical site and containing the tissue specimen "S" to be broken down and removed therein.

With elongated tubular member 6100 inserted as detailed above, grasper 6200 may be manipulated to grasp the tissue specimen "S" with working end 6210 thereof to thereby maintain the tissue specimen "S" substantially stationary relative to elongated tubular member 6100 and grasper 6200.

With the tissue specimen "S" retained in position, cutting element 6300, if not done so already, may be advanced distally to the distal position and tissue-strip cutting device 6000 manipulated such that a portion of the tissue specimen "S" is disposed between U-shaped loop 6320 of cutting element 6300 and the distal end of elongated tubular member 6100. Once cutting element 6300 has reached the distal position (or a sufficiently-distal position such that a portion of the tissue specimen "S" is disposed between U-shaped loop 6320 and elongated tubular member 6100), cutting element 6300 is energized and translated proximally relative to elongated tubular member 6100, grasper 6200, and, thus, the tissue specimen "S." As a result, a smaller tissue strip "SS" is electromechanically cut from the tissue specimen "S."

The above-detailed cutting of smaller tissue strips "SS" from the tissue specimen "S" may be repeated until the remaining portion of the tissue specimen "S" is sufficiently small so as to allow for minimally-invasive removal. The smaller tissue strips "SS" may be removed, one or more at a time, through elongated tubular member 6100, e.g., using grasper 6200, or may be removed together with the containment bag 300 (FIGS. 8E-8H).

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of containing a tissue specimen disposed within an internal body cavity, comprising:
   inserting a cannula arrangement through a vagina and into a pelvic cavity, wherein the cannula arrangement includes an access cannula, a deployment cannula slidably disposed within the access cannula, a deployment plunger having a plurality of engagement arms slidably disposed within a first annular space defined between the access cannula and the deployment cannula, and an inner cannula slidably disposed within the deployment cannula, and wherein a containment bag is disposed within the cannula arrangement;

distally advancing the deployment cannula relative to the access cannula to deploy a first portion of the containment bag from the cannula arrangement, in the pelvic cavity, and at least partially about a tissue specimen; and distally advancing the deployment plunger relative to the deployment cannula and the access cannula to deploy a second portion of the containment bag from the cannula arrangement and into the pelvic cavity such that the containment bag is further disposed about the tissue specimen.

2. The method according to claim 1, further comprising:
proximally withdrawing the inner cannula from the deployment cannula; and
reinserting the inner cannula distally through the deployment cannula to deploy a third portion of the containment bag from the cannula arrangement and into the pelvic cavity.

3. The method according to claim 1, further comprising withdrawing the first portion of the containment bag from the pelvic cavity through an abdominal port.

4. The method according to claim 1, further comprising:
inserting a tenaculum or a grasper through the inner cannula; and
grasping the specimen with the tenaculum or grasper to maintain the specimen in position or pull the specimen proximally during deployment of at least one of the first or second portions of the containment bag.

5. The method according to claim 1, further comprising:
proximally withdrawing the inner cannula; and
inserting a morcellator through the deployment cannula and into the pelvic cavity within the containment bag.

6. The method according to claim 5, wherein an insert portion of the deployment cannula is replaced with a different insert portion after proximally withdrawing the inner cannula and before inserting the morcellator.

* * * * *